US012245810B2

(12) United States Patent
Carroll et al.

(10) Patent No.: US 12,245,810 B2
(45) Date of Patent: Mar. 11, 2025

(54) METHODS AND APPARATUS FOR EVALUATING VISUAL ACUITY OF TELEOPERATION VISION SYSTEMS AND SIMULATION SYSTEMS

(71) Applicant: Nuro, Inc., Mountain View, CA (US)

(72) Inventors: Benjamin Caleb Carroll, San Francisco, CA (US); Gulnara Ghorbanian, San Jose, CA (US); Scott Edward Slattery, Mountain View, CA (US); Lifan Zeng, Troy, MI (US); Qingyang Chen, San Jose, CA (US)

(73) Assignee: NURO, INC., Mountain View, CA (US)

( * ) Notice: Subject to any disclaimer, the term of this patent is extended or adjusted under 35 U.S.C. 154(b) by 798 days.

(21) Appl. No.: 17/461,090

(22) Filed: Aug. 30, 2021

(65) Prior Publication Data

US 2022/0061651 A1 Mar. 3, 2022

Related U.S. Application Data

(60) Provisional application No. 63/110,061, filed on Nov. 5, 2020, provisional application No. 63/072,684, filed on Aug. 31, 2020.

(51) Int. Cl.
A61B 3/032 (2006.01)
A61B 5/18 (2006.01)
(Continued)

(52) U.S. Cl.
CPC ............... *A61B 3/032* (2013.01); *A61B 5/18* (2013.01); *G06T 7/80* (2017.01); *G16H 40/67* (2018.01)

(58) Field of Classification Search
CPC .......... A61B 3/032; A61B 5/18; A61B 3/028; G06T 7/80; G16H 40/67
See application file for complete search history.

(56) References Cited

U.S. PATENT DOCUMENTS 10,758,120 B2 * 9/2020 Lesmes ................... A61B 3/00
2022/0369921 A1 * 11/2022 Sakurada ............. A61B 3/0033

FOREIGN PATENT DOCUMENTS

KR 101776717 B1 9/2017
WO WO2014126307 A1 8/2014

OTHER PUBLICATIONS

ASTM International, "Standard Test Method for Evaluating Response Robot Sensing: Visual Acuity", Sep. 2017.
(Continued)

Primary Examiner — Tuyen Tra
(74) Attorney, Agent, or Firm — Edell, Shapiro & Finnan, LLC

(57) ABSTRACT

According to one aspect, a method for validating a vision system includes providing a vision testing medium at a first distance from the vision system, communicating a first information relating to the vision testing medium from the sensing apparatus to a first system, and displaying, using the first system, a rendering of the vision testing medium based on the first information. The method also includes obtaining, using the first system, at least a first indication of a visual acuity associated with the vision system, determining when the visual acuity at least meets a threshold level, and identifying the sensing apparatus as validated when the visual acuity at least meets the threshold level.

20 Claims, 17 Drawing Sheets

(51) Int. Cl.
  *G06T 7/80* (2017.01)
  *G16H 40/67* (2018.01)

(56) References Cited

OTHER PUBLICATIONS

Matts, Tobias, "Vision-based Driver Assistance Systems for Teleoperation of OnRoad Vehicles", https://www.diva-portal.org/smash/get/diva2:1448551/FULLTEXT01.pdf, May 28, 2020.

* cited by examiner

METHODS AND APPARATUS FOR EVALUATING VISUAL ACUITY OF TELEOPERATION VISION SYSTEMS AND SIMULATION SYSTEMS

PRIORITY CLAIM

This patent application claims the benefit of priority under 35 U.S.C. § 119 to U.S. Provisional Patent Application No. 63/072,684, filed Aug. 31, 2020 and entitled "METHODS AND APPARATUS FOR ASSESSING VISUAL ACUITY OF TELEOPERATION VISION SYSTEMS," and to U.S. Provisional Patent Application No. 63/110,061, filed Nov. 5, 2020 and entitled "METHODS AND APPARATUS FOR EVALUATING VISUAL ACUITY OF TELEOPERATION VISION SYSTEMS," which are each incorporated herein by reference in their entireties.

TECHNICAL FIELD

The disclosure relates to providing systems for use with autonomous vehicles. More particularly, the disclosure relates to a system that facilitates the validation of a teleoperation system used with autonomous vehicles.

BACKGROUND

Teleoperation systems are often used to remotely operate vehicles, as for example when an autonomous vehicle is unable to operate safely without assistance from a remote human operator. In order for a teleoperation system to be used to safely operate a remote vehicle, a vision system which provides a view of the environment in which the vehicle is driving must generally provide high quality video. That is, a vision system used by a teleoperation system to remotely operate a vehicle must provide video of at least a certain, e.g., minimum, resolution or sharpness.

BRIEF DESCRIPTION OF THE DRAWINGS

The disclosure will be readily understood by the following detailed description in conjunction with the accompanying drawings in which.

DESCRIPTION OF EXAMPLE EMBODIMENTS

General Overview

Figure 1:
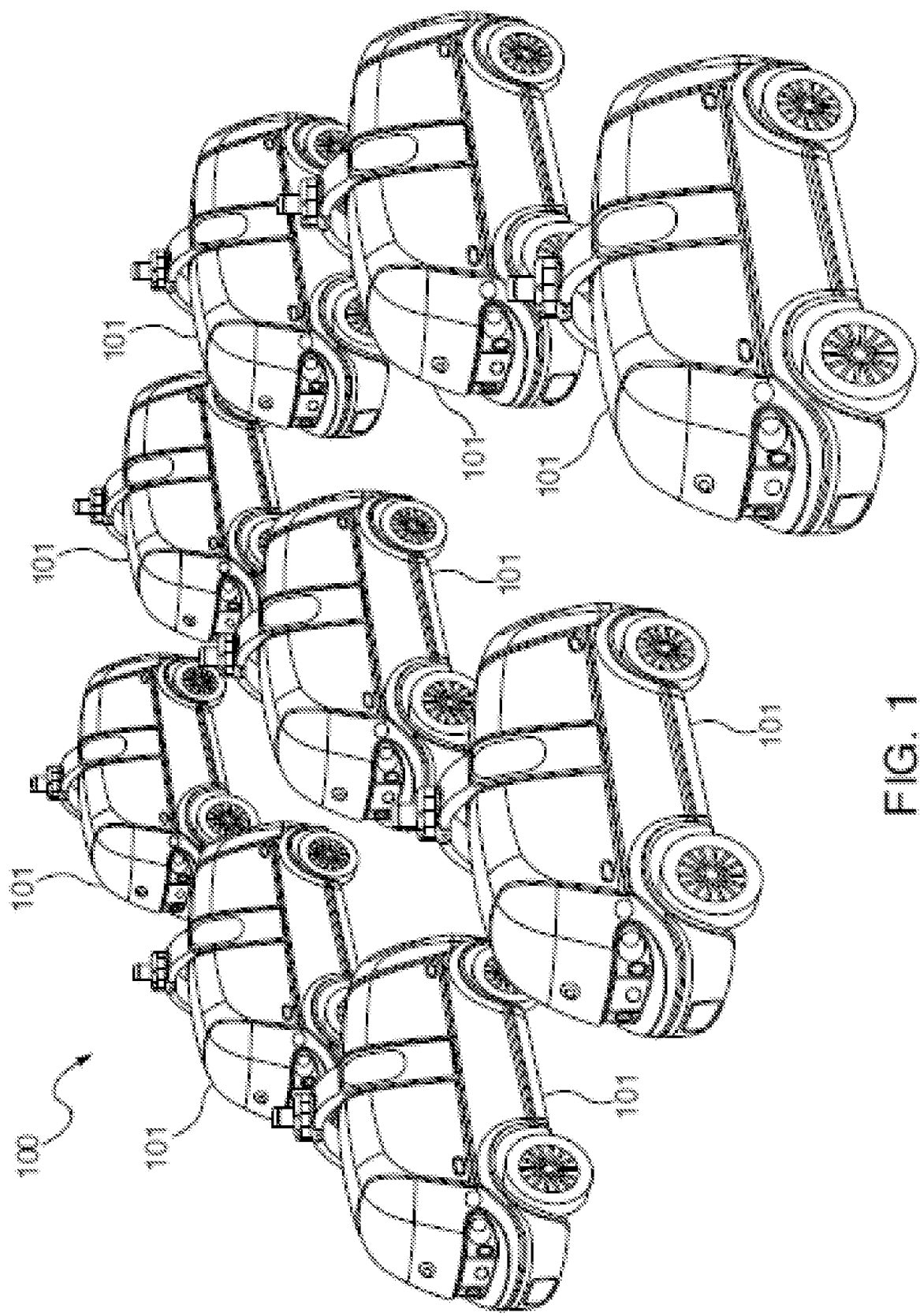
FIG. 1 is a diagrammatic representation of an autonomous vehicle fleet in accordance with an embodiment.

In one embodiment, a method for validating a vision system includes providing a vision testing medium at a first distance from the vision system, communicating a first information relating to the vision testing medium from the sensing apparatus to a first system, and displaying, using the first system, a rendering of the vision testing medium based on the first information. The method also includes obtaining, using the first system, at least a first indication of a visual acuity associated with the vision system, determining when the visual acuity at least meets a threshold level, and identifying the sensing apparatus as validated when the visual acuity at least meets the threshold level.

In another embodiment, logic is encoded in one or more tangible non-transitory, computer-readable media for execution. When executed, the logic is operable to provide a vision testing medium at a first distance from the vision system, to communicate a first information relating to the vision testing medium from the sensing apparatus to a first system, and to display, using the first system, a rendering of the vision testing medium based on the first information. The logic is further operable to obtain, using the first system, at least a first indication of a visual acuity associated with the vision system, to determine when the visual acuity at least meets a threshold level; and to identify the sensing apparatus as validated when the visual acuity at least meets the threshold level.

In yet another embodiment, a method includes obtaining a first information from a simulation system, the simulation system configured to simulate a driving environment, the first information including a first indication associated with a vision testing medium rendered using the simulation system, the first information being arranged to indicate a visual acuity associated with the simulation system. The method also includes comparing the first information to a visual acuity associated with a vision system of a vehicle. Comparing the first information to the visual acuity associated with the vision system of the vehicle includes determining whether the first information indicates at least an approximate match between the visual acuity associated with the simulation system and the visual acuity associated with the vision system of the vehicle. Finally, the method includes adjusting at least one parameter associated with the simulation system when it is determined that the first information does not indicate the at least approximate match between the visual acuity associated with the simulation system and the visual acuity associated with the vision system of the vehicle, and identifying the simulation system as calibrated when it is determined that the first information indicates the at least approximate match between the visual acuity associated with the simulation system and the visual acuity associated with the vision system of the vehicle.

In still another embodiment, a vision system associated with a teleoperation system is effectively validated through the use of at least one vision acuity test. A vision system, which may include cameras and/or other sensors arranged to provide a visual depiction of an environment, may be used provide a photograph or a video of a vision testing medium to a human via a teleoperations system. The vision testing medium may be an eye chart, e.g., a Landolt C eye chart. A human may view the vision testing medium using the teleoperations system. Different components of the vision system may be tested by placing the eye chart at different locations relative to the vision system, as for example such that the human may effectively see what the vision system sees with respect to different sides of the vehicle. The performance of the human when reading or otherwise deciphering the vision testing medium may be assessed to determine whether the vision system meets standards. When the performance meets standards set for human drivers, as for example when human drivers are tested when applying for or renewing drivers licenses, then a vision system and, hence, a teleoperations system may be considered to be validated.

DESCRIPTION

As the use of autonomous vehicles grows, the ability for the autonomous vehicles to operate safely is becoming increasingly important. Teleoperation systems are often used to facilitate the safe operation of autonomous vehicles. A teleoperation system may be used to remotely operate an autonomous vehicle when the autonomous vehicle in need of assistance, as for example when the autonomous vehicle is unable to safely navigate a particular roadway or otherwise respond to an unexpected situation. Other systems such as simulation systems are used to increase the likelihood that when autonomous vehicles are operating on roads, the autonomous vehicles are operating safely.

In order for a teleoperation system to take control of a vehicle when an autonomy system of the vehicle effectively relinquishes control to the teleoperation system, video or other vision data provided by the vehicle to the teleoperation system is used by the teleoperation system to substantially navigate the vehicle. If the video or vision data is not of an adequate resolution or quality to enable a teleoperator, or a remote human driver, to safely operate the vehicle, then the vehicle may pose a danger in its environment. Thus, it is important to essentially ensure that the video or vision data provided to a teleoperation system by a vehicle, or by a vision system of the vehicle, meets acceptable standards.

In one embodiment, the vision system of an autonomous vehicle may effectively be calibrated using one or more vision testing mediums that are generally used to test human vision. A vision testing medium may be an eye chart such as a Landolt C eye chart, or a Landolt eye chart, that is placed at a predetermined distance from a vision system of a vehicle, and a visual image of the vision testing medium may be transmitted to a teleoperation system. A human may view the visual image using the vision system of the vehicle, and if the human is able to accurately discern the vision testing medium in the visual image, then the vision system may be determined to meet acceptable standards. In other words, a human who may remotely operate a vehicle using a teleoperation system may effectively be tested in the same way that he or she would be tested to be licensed to drive a vehicle from a cockpit or a driver's seat.

By essentially administering an eye test to a human using a vision system of an autonomous vehicle in cooperation with a teleoperations system, the vision system may be substantially validated. For example, a vision testing medium may be positioned with respect to a vision system that is such that a human who is viewing the vision testing medium through a teleoperation system is effectively viewing the vision testing medium from a distance of approximately twenty feet. If the human has vision that meets predetermined standards for a static visual acuity as determined using the vision testing medium, then the vision system may be considered to be validated. While some standards may specify that a human needs to test as having substantially perfect vision in terms of clearness and sharpness of vision, e.g., approximately 20/20 vision, in order to safely operate a vehicle, other standards may specify that a human may be deemed able to safely operate a vehicle with less than perfect vision, e.g., approximately 20/40 vision. In general, if a human is able to clearly and sharply discern the vision testing medium transmitted to a display screen by a vision system, then the vision system may be considered to be validated.

In one embodiment, a vision testing medium may be a Landolt eye test chart or a Landolt C eye chart, although it should be appreciated that the vision testing medium is not limited to being a Landolt eye chart or a Landolt C eye chart, A Landolt eye chart includes at least one Landolt C. That is, a Landolt eye chart includes optotypes that are Landolt C's. Landolt C is typically a circle or a ring that has an opening or a gap within the ring such that the Landolt C approximates the letter "C." A Landolt C, which may also be known as a Landolt ring, a Landolt broken ring, or a broken ring, may be rotated such that the gap may be in different positions with respect to the ring that includes the gap. For example, the gap may be located at approximately zero degrees or in an "up" position, approximately 90 degrees or in a "right position," approximately 180 degrees or in a "down position," and/or approximately 270 degrees or in a "left position" along the ring. Generally, a substantially minimum perceivable angle of the gap may be considered to be a measurement of visual acuity, A Landolt eye chart may be positioned at a distance away from a vision system that, when calibrated with respect to a distance between a human and a teleoperations system, provides an effective distance of approximately twenty feet between the Landolt C eye chart and the human. In one embodiment, a Landolt eye chart may be positioned at a distance of approximately twenty feet away from a vision system of a vehicle, and an individual viewing the Landolt eye chart using a display screen of a teleoperations system may be considered to be viewing the Landolt eye chart from approximately twenty feet away. Alternatively, a distance between an individual and a display screen of a teleoperations system may be accounted for when determining how many feet away from a vision system of a vehicle a Landolt eye chart is to be positioned in order for the individual to effectively be considered to be viewing the Landolt eye chart from a distance of approximately twenty feet.

Visual acuity, in one embodiment, is a measure of a spatial resolution of an optical system. For example, visual acuity may be defined for the human eye as a function of a gap size, or a testing distance. A visual acuity "score" for a human may measure an ability of the human to resolve detail in a scene, image, or object. For example, the smallest optotype within which an individual may identify or otherwise recognize a critical detail may substantially determine a visual acuity score of the individual. A visual acuity score for an individual, as defined with respect to a Landolt eye test, may be based upon the smallest "C" for which the individual ay identify a location of a gap, which may be considered to be a critical detail.

An autonomous vehicle that may be operated using a teleoperation system may generally be part of a fleet of autonomous vehicles. Referring initially to FIG. 1, an autonomous vehicle fleet will be described in accordance with an embodiment. An autonomous vehicle fleet 100 includes a plurality of autonomous vehicles 101, or robot vehicles. Autonomous vehicles 101 are generally arranged to transport and/or to deliver cargo, items, and/or goods. Autonomous vehicles 101 may be fully autonomous and/or semi-autonomous vehicles. In general, each autonomous vehicle 101 may be a vehicle that is capable of travelling in a controlled manner for a period of time without intervention, e.g., without human intervention. As will be discussed in more detail below, each autonomous vehicle 101 may include a power system, a propulsion or conveyance system, a navigation module, a control system or controller, a communications system, a processor, and a sensor system.

Dispatching of autonomous vehicles 101 in autonomous vehicle fleet 100 may be coordinated by a fleet management module (not shown). The fleet management module may dispatch autonomous vehicles 101 for purposes of transporting, delivering, and/or retrieving goods or services in an unstructured open environment or a closed environment.

Figure 2:
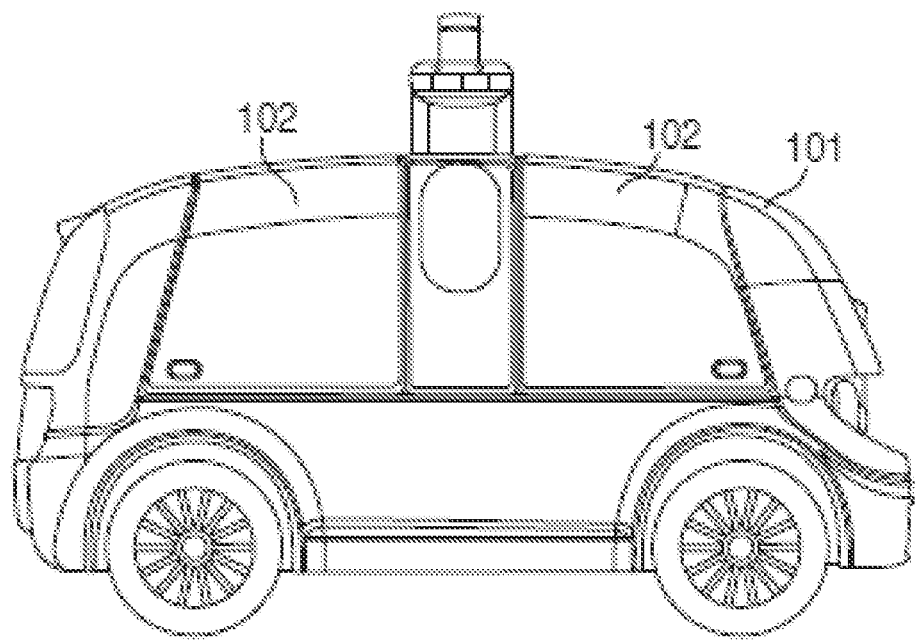
FIG. 2 is a diagrammatic representation of a side of an autonomous vehicle in accordance with an embodiment.

FIG. 2 is a diagrammatic representation of a side of an autonomous vehicle, e.g., one of autonomous vehicles 101 of FIG. 1, in accordance with an embodiment. Autonomous vehicle 101, as shown, is a vehicle configured for land travel. Typically, autonomous vehicle 101 includes physical vehicle components such as a body or a chassis, as well as conveyance mechanisms, e.g., wheels. In one embodiment, autonomous vehicle 101 may be relatively narrow, e.g., approximately two to approximately five feet wide, and may have a relatively low mass and relatively low center of gravity for stability. Autonomous vehicle 101 may be arranged to have a working speed or velocity range of between approximately one and approximately forty-five miles per hour (mph), e.g., approximately twenty-five miles per hour. In some embodiments, autonomous vehicle 101 may have a substantially maximum speed or velocity in range between approximately thirty and approximately ninety mph.

Autonomous vehicle 101 includes a plurality of compartments 102. Compartments 102 may be assigned to one or more entities, such as one or more customer, retailers, and/or vendors. Compartments 102 are generally arranged to contain cargo, items, and/or goods. Typically, compartments 102 may be secure compartments. It should be appreciated that the number of compartments 102 may vary. That is, although two compartments 102 are shown, autonomous vehicle 101 is not limited to including two compartments 102.

Figure 3:
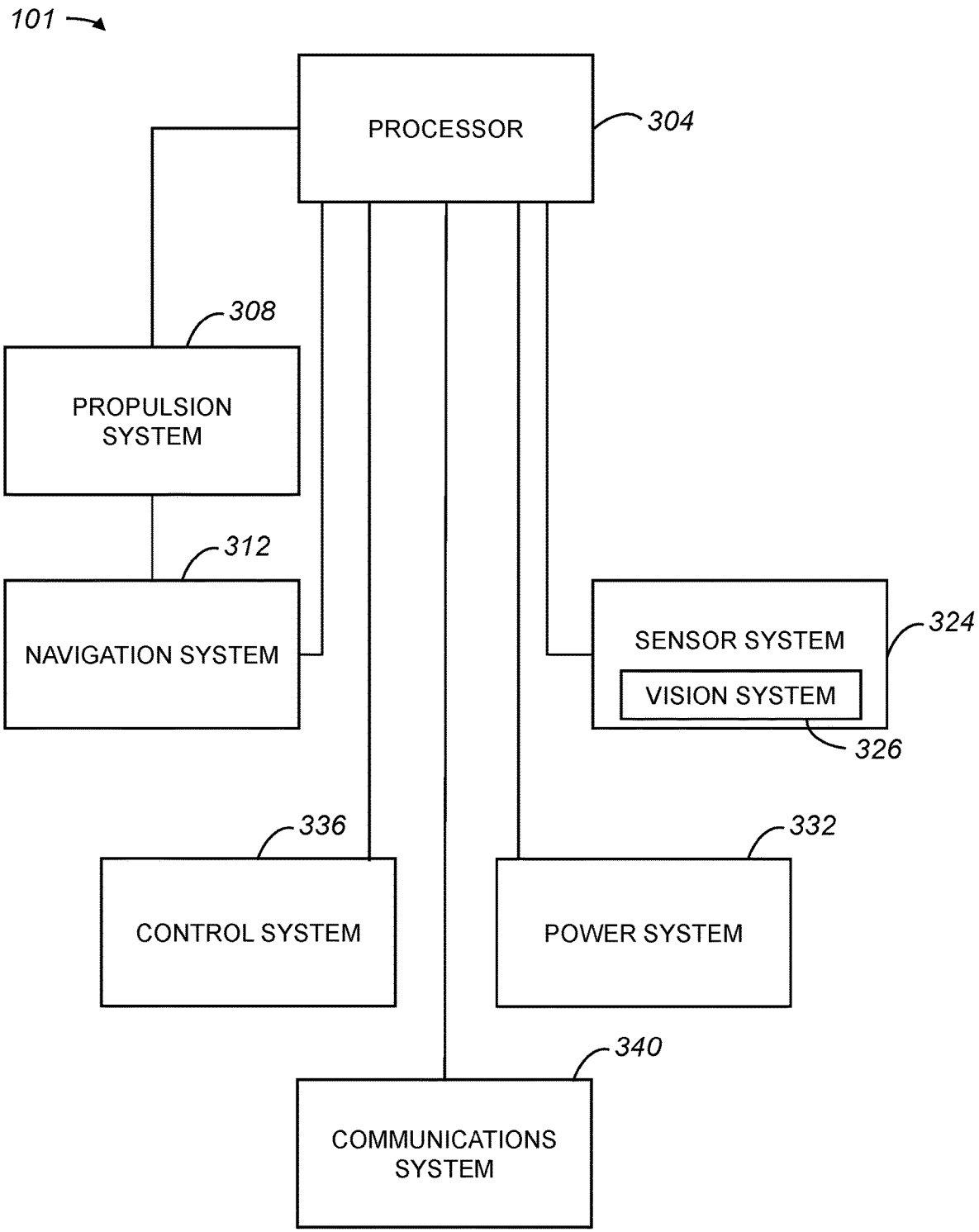
FIG. 3 is a block diagram representation of an autonomous vehicle in accordance with an embodiment.

FIG. 3 is a block diagram representation of an autonomous vehicle, e.g., autonomous vehicle 101 of FIG. 1, in accordance with an embodiment. An autonomous vehicle 101 includes a processor 304, a propulsion system 308, a navigation system 312, a sensor system 324, a power system 332, a control system 336, and a communications system 340. It should be appreciated that processor 304, propulsion system 308, navigation system 312, sensor system 324, power system 332, and communications system 340 are all coupled to a chassis or body of autonomous vehicle 101.

Processor 304 is arranged to send instructions to and to receive instructions from or for various components such as propulsion system 308, navigation system 312, sensor system 324, power system 332, and control system 336. Propulsion system 308, or a conveyance system, is arranged to cause autonomous vehicle 101 to move, e.g., drive. For example, when autonomous vehicle 101 is configured with a multi-wheeled automotive configuration as well as steering, braking systems and an engine, propulsion system 308 may be arranged to cause the engine, wheels, steering, and braking systems to cooperate to drive. In general, propulsion system 308 may be configured as a drive system with a propulsion engine, wheels, treads, wings, rotors, blowers, rockets, propellers, brakes, etc. The propulsion engine may be a gas engine, a turbine engine, an electric motor, and/or a hybrid gas and electric engine.

Navigation system 312 may control propulsion system 308 to navigate autonomous vehicle 101 through paths and/or within unstructured open or closed environments. Navigation system 312 may include at least one of digital maps, street view photographs, and a global positioning system (GPS) point. Maps, for example, may be utilized in cooperation with sensors included in sensor system 324 to allow navigation system 312 to cause autonomous vehicle 101 to navigate through an environment.

Sensor system 324 includes any sensors, as for example LiDAR, radar, ultrasonic sensors, microphones, altimeters, and/or cameras. Sensor system 324 generally includes onboard sensors which allow autonomous vehicle 101 to safely navigate, and to ascertain when there are objects near autonomous vehicle 101. In one embodiment, sensor system 324 may include propulsion system sensors that monitor drive mechanism performance, drive train performance, and/or power system levels. Sensor system 324 includes a vision system 326 that may include sensors such as cameras and/or other sensors which may effectively obtain visual information. Vision system 324 may provide information to remote systems (not shown) such as a teleoperation system via communications system 340. A teleoperation system (not shown) may be used to remotely operate vehicle 101 remotely by providing input, via communications system 340, to systems of vehicle 101 such as propulsion system 308 and navigation system 312. In one embodiment, an assessment of whether vision system 326 may provide a relatively accurate view of the environment around vehicle 101 to a teleoperation system (not shown) may be made using a visual acuity test such as a Landolt eye test. Such a visual acuity test may be used to test different components or aspects of vision system 326, e.g., the visual acuity test and vision system 326 may be moved relative to each other such that different components or aspects may be substantially evaluated.

Power system 332 is arranged to provide power to autonomous vehicle 101. Power may be provided as electrical power, gas power, or any other suitable power, e.g., solar power or battery power. In one embodiment, power system 332 may include a main power source, and an auxiliary power source that may serve to power various components of autonomous vehicle 101 and/or to generally provide power to autonomous vehicle 101 when the main power source does not have the capacity to provide sufficient power.

Communications system 340 allows autonomous vehicle 101 to communicate, as for example, wirelessly, with a fleet management system (not shown) that allows autonomous vehicle 101 to be controlled remotely. Communications system 340 generally obtains or receives data, stores the data, and transmits or provides the data to a fleet management system and/or to autonomous vehicles 101 within a fleet 100. The data may include, but is not limited to including, information relating to scheduled requests or orders, information relating to on-demand requests or orders, and/or information relating to a need for autonomous vehicle 101 to reposition itself, e.g., in response to an anticipated demand.

In some embodiments, control system 336 may cooperate with processor 304 to determine where autonomous vehicle 101 may safely travel, and to determine the presence of objects in a vicinity around autonomous vehicle 101 based on data, e.g., results, from sensor system 324. In other words, control system 336 may cooperate with processor 304 to effectively determine what autonomous vehicle 101 may do within its immediate surroundings. Control system 336 in cooperation with processor 304 may essentially control power system 332 and navigation system 312 as part of driving or conveying autonomous vehicle 101. Additionally, control system 336 may cooperate with processor 304 and communications system 340 to provide data to or obtain data from other autonomous vehicles 101, a management server, a global positioning server (GPS), a personal computer, a teleoperations system, a smartphone, or any computing device via the communication module 340. In general, control system 336 may cooperate at least with processor 304, propulsion system 308, navigation system 312, sensor system 324, and power system 332 to allow vehicle 101 to operate autonomously. That is, autonomous vehicle 101 is able to operate autonomously through the use of an autonomy system that effectively includes, at least in part, functionality provided by propulsion system 308, navigation system 312, sensor system 324, power system 332, and control system 336.

As will be appreciated by those skilled in the art, when autonomous vehicle 101 operates autonomously, vehicle 101 may generally operate, e.g., drive, under the control of an autonomy system. That is, when autonomous vehicle 101 is in an autonomous mode, autonomous vehicle 101 is able to generally operate without a driver or a remote operator controlling autonomous vehicle. In one embodiment, autonomous vehicle 101 may operate in a semi-autonomous mode or a fully autonomous mode. When autonomous vehicle 101 operates in a semi-autonomous mode, autonomous vehicle 101 may operate autonomously at times and may operate under the control of a driver or a remote operator at other times. When autonomous vehicle 101 operates in a fully autonomous mode, autonomous vehicle 101 typically operates substantially only under the control of an autonomy system. The ability of an autonomous system to collect information and extract relevant knowledge from the environment provides autonomous vehicle 101 with perception capabilities. For example, data or information obtained from sensor system 324 may be processed by a perception system such that the environment around autonomous vehicle 101 may effectively be perceived.

In order to ensure that vehicle 101 may be controlled by a teleoperator, or a remote driver using a teleoperation system, vision system 326 may be tested or calibrated to substantially ensure that vision system 326 is capable of providing clear and sharp images. A teleoperation system may be used, in one embodiment, to facilitate the validation of the visual acuity of vision system 326.

Figure 4:
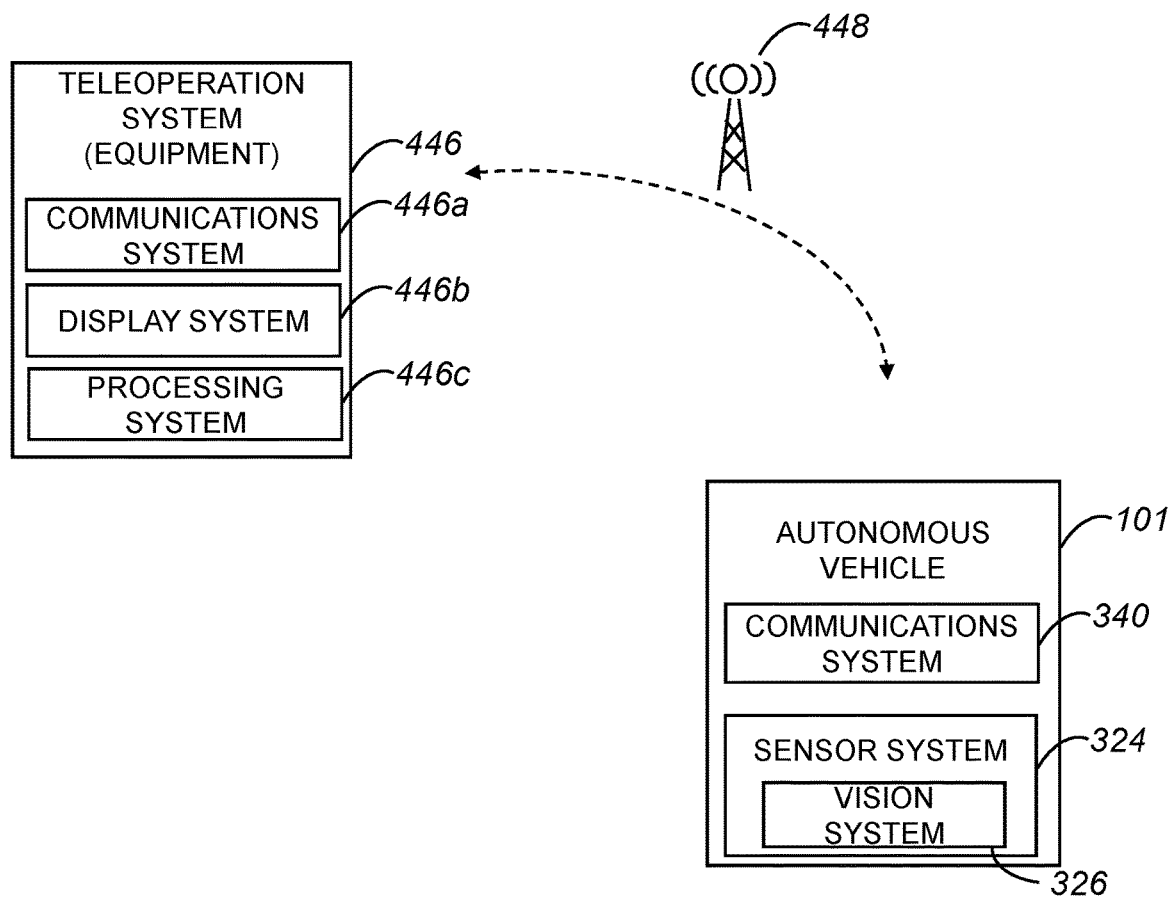
FIG. 4 is a block diagram representation of an overall system which allows for the visual acuity of a vision system to be validated in accordance with an embodiment.

With reference to FIG. 4, an overall system which allows for the visual acuity of a vision system to be validated will be described in accordance with an embodiment. An overall system 442 that facilitates the validation of a vision system on an autonomous vehicle includes autonomous vehicle 101 and a teleoperation system or equipment 446 which communicate over a network 448. Network 448 may be, but is not limited to being, a wireless network such as a cellular network, e.g., an LTE network and/or a 3G/4G/5G network, a Wi-Fi network, and/or a Bluetooth network.

Teleoperation system 446 is configured to be used to remotely operate or otherwise control autonomous vehicle 101, as for example when vehicle 101 is unable to safely operate in an autonomous mode. Teleoperation system 446 generally includes equipment such as an operator station that includes ate least a steering wheel, acceleration and brake pedals, and a gear shifter. That is, teleoperation system 446 includes equipment which enables an individual to remotely drive autonomous vehicle 101. Teleoperation system 446 also includes a communications system 446a, a display system 446b, and a processing system 466c. Communications system 446a is arranged to enable teleoperation system 446 to communicate with autonomous vehicle 101 through network 448. Display system 446b is arranged to display data, e.g., visual information received from or otherwise obtained from vision system 326 of vehicle 101. Processing system 446c is arranged to process signals generated by teleoperation system 446 such as signals from an operator station, and to translate the signals into control instructions for substantially controlling autonomous vehicle 101. Processing system 446c may cooperate with communications system 446a to provide teleoperation capabilities.

Vehicle 101 communicates with teleoperation system 446 through communications system 340. Data, i.e., image data or visual data, obtained through sensor system 324 may be provided through communications system 340 and network 448 to communications system 446a. For example, a signal which contains information from vision system 326 may be provided for display on display system 446b. Once information such as images from vision system 326 are presented to a human who view display system 446b, the human may determine whether he or she is able to see the images clearly and sharply.

Figure 5:
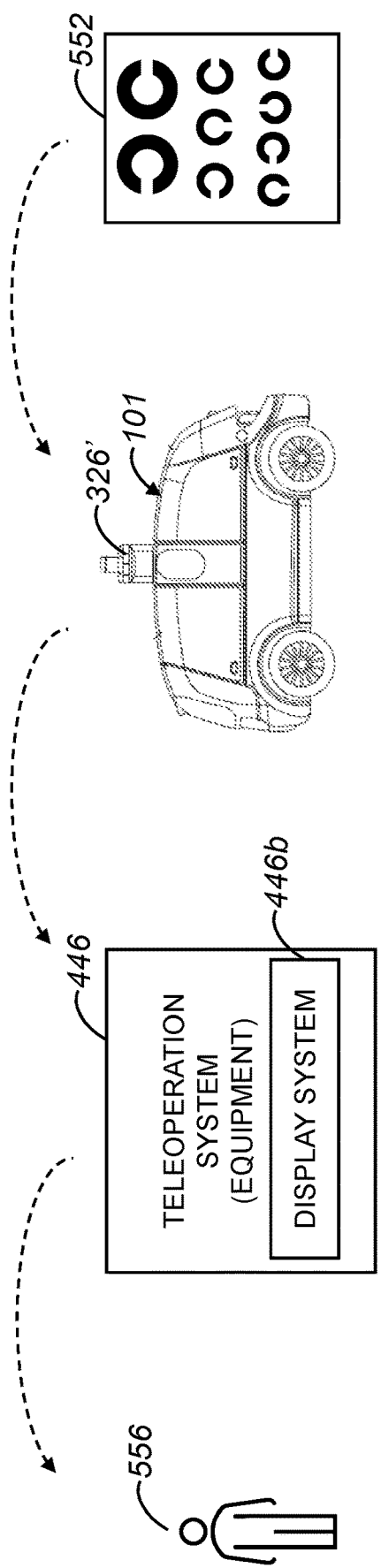
FIG. 5 is a diagrammatic representation of a system which facilitates the validation of a vision system of a vehicle using an eye chart, e.g., a Landolt eye chart, and a human in accordance with an embodiment.

FIG. 5 is a diagrammatic representation of a system which facilitates the validation of a vision system of a vehicle using an eye chart and a human in accordance with an embodiment. A vision test medium 552, which may be an eye test chart such as a Landolt test chart, may be positioned within range of a vision system 326' of autonomous vehicle 101. Vision system 326' may provide an image of vision test medium 552 to display system 446b of teleoperations system 446, and an individual 556 may view the image to determine how clearly and sharply he or she is able to see the image, or at least the portion of the image which depicts vision test medium 552.

The actual distance between vision system 326' and vision test medium 552 may be determined using a variety of suitable criteria. Suitable criteria may include, but are not limited to including, an effective distance from which individual 556 is to be from vision test medium 552, an actual size of vision test medium 552, the quality of display system 446b of teleoperations system 446, etc. In one embodiment, when vision test medium 552 is a Landolt eye test chart, vision test medium 552 may be positioned at a specified distance in front of vision system 326', with the specified distance being a function of the sizes of each Landolt C included in vision test medium 552. The specified distance may be a distance of up to approximately twenty feet in some embodiments, although it should be understood that the distance may vary widely based on the sizes of each Landolt C in vision test medium 552.

It should be appreciated that when vision test medium 552 is positioned at a predetermined distance in front of vision system 326', visual acuity may be measured in terms of 20/20 vision, 20/40 vision, etc., and it may be determined that individual 556, when viewing an image of vision test medium 552 on display system 446, is effectively viewing the image from a distance at which a person with 20/20 vision may see the image clearly. For example, vision test medium 552 may be positioned twenty feet in front of vision system 326' such that if individual 556 is able to view an image of vision test medium 552 clearly, visual acuity may be substantially determined to be 20/20. In another embodiment, vision test medium 552 may be positioned at a distance from vision system 326' such that, together with a distance between individual 556 and teleoperation system 446, an overall effective viewing distance between individual 556 and vision test medium 552 may be a predetermined distance that correlates to a distance from which a person with 20/20 vision may see the image clearly.

When individual 556 views an image of vision test medium 552 using display system 446b, individual 556 is effectively determining the visual acuity of vision system 326'. If individual 556 has substantially perfect vision, e.g., approximately 20/20 vision, then individual 556 may generally be able to accurately identify critical features such as a gap in each Landolt C displayed on vision test medium 552 that he or she is expected to be able to discern, as for example from an effective distance of approximately twenty feet. As such, visual acuity of vision system, 326' may effectively be validated when individual 556 may accurately identify critical features. In other words, if individual 556 is able to clearly and sharply discern vision test medium 552, e.g., identify critical features in each Landolt C associated with vision test medium 552, when viewed on display system 446b, then vision system 326' may effectively be validated.

As mentioned above, a vision system such as vision system 326 of FIG. 3 may include various components. For example, vision system 326 may include a plurality of sensors including, but not limited to including, cameras, lidars, and/or radars. Sensors within vision system 326 may generally be located substantially anywhere on or within a vehicle such as vehicle 101 of FIGS. 2 and 3. Although vision system 326' is shown as being located substantially atop vehicle 101, it should be appreciated that in general, components of vision system 326' are not limited to being located substantially atop vehicle 101, and may be located in a variety of different positions on or within vehicle 101.

In one embodiment, a vision system may include sensors which are oriented to substantially face different directions. By way of example, a vision system may include cameras or other vision sensors which face forward, face to the right, face backward, and face to the left of a vehicle. In order to determine the visual acuity of such cameras or other vision sensors, a vision test may be substantially administered using each of the cameras or other vision sensors. A vehicle and/or a visual acuity test such as a Landolt eye chart may be arranged to be moved such that different sensors may be evaluated by the visual acuity test. That is, the visual acuity of sensors on different sides with respect to a vision system may be evaluated by moving the vehicle relative to a Landolt eye chart, by moving the Landolt eye chart relative to the vehicle, or both.

Figure 6A:
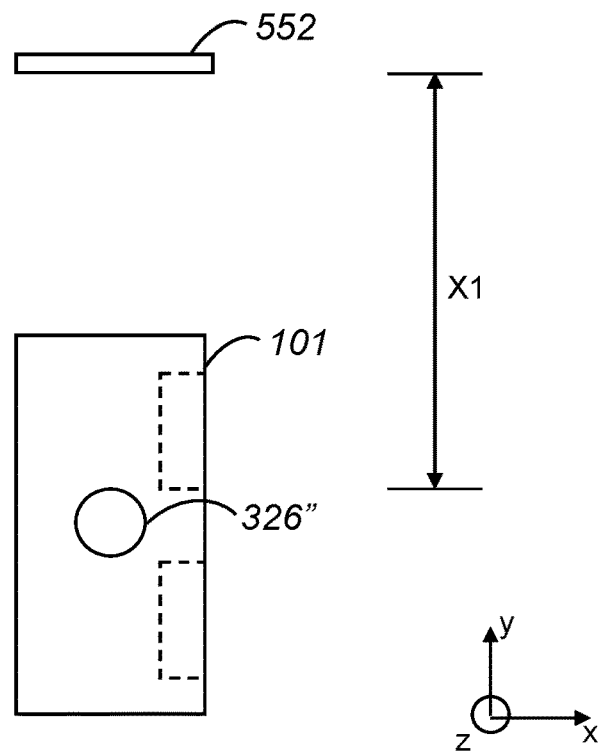
FIG. 6A is a diagrammatic representation of a vehicle in a first orientation with respect to an eye chart in accordance with an embodiment.

With reference to FIGS. 6A-D, the performance of visual acuity tests for different sensors included in a vision system will be described in accordance with an embodiment. FIG. 6A is a diagrammatic representation of a vehicle in a first orientation with respect to an eye chart in accordance with an embodiment. Vehicle 101 includes a vision system 326" which includes a plurality of cameras and/or other vision sensors. While vision system 326" may be located at a substantially single area of vehicle 101, as shown, it should be appreciated that vision system 326" may instead be distributed with respect to vehicle 101, e.g., vision system 326" may include different components which are substantially spread out with respect to vehicle 101.

Visual acuity test 552, which may be a Landolt eye test, is arranged at a distance X1 from a substantially front edge associated with vision system 326". When vehicle 101 is oriented with a front edge associated with vision system 326" that essentially faces visual acuity test 552, an image of visual acuity test 552 that is captured by vision system 326" may effectively be used to determine a visual acuity associated with a sensor of vision system 326" that is generally front-facing.

Distance X1 may be, in one embodiment, a distance from visual acuity test 552 to a front edge associated vision system 326" that effectively enables an individual (not shown) who is viewing visual acuity test 552 through a display screen of a teleoperations system (not shown) to see visual acuity test 552 as if he or she is viewing visual acuity test 552 from a predetermined distance associated with substantially perfect visual acuity, e.g., from approximately twenty feet away. Distance X1 may, however, vary depending upon factors including, but not limited to including, a size of optotypes on visual acuity test 552, a distance between an individual and a display screen, and/or a quality of the display screen.

Figure 6B:
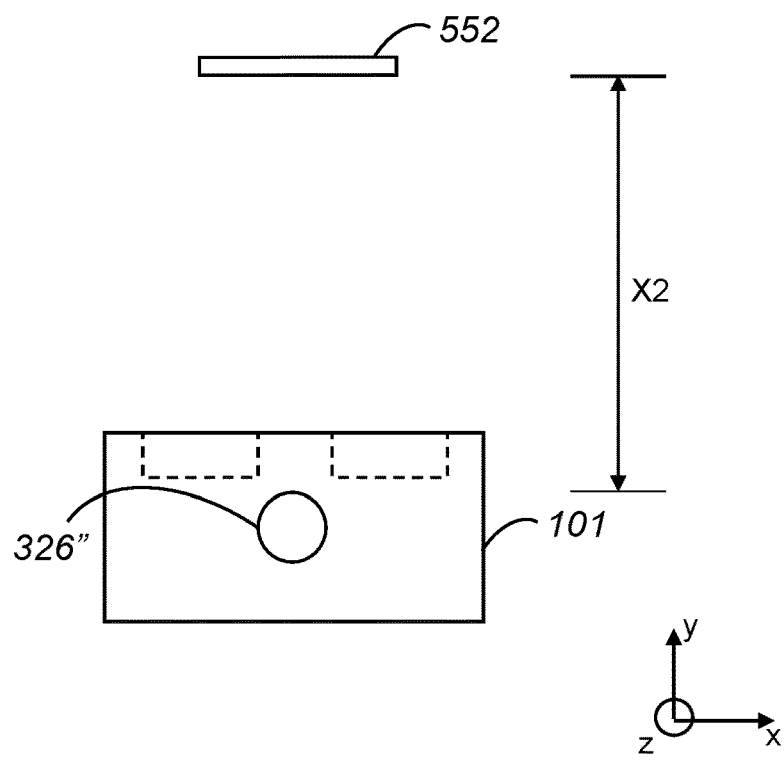
FIG. 6B is a diagrammatic representation of a vehicle in a second orientation with respect to an eye chart in accordance with an embodiment.

In order to evaluate the visual acuity associated with a first side of vehicle 101, e.g., a right side of vehicle 101, either vehicle 101 or visual acuity test 552 may be moved such that a first side of vehicle 101 may substantially face visual acuity test 552. FIG. 6B is a representation of vehicle 101 in a second orientation in which a first side of vehicle 101 substantially faces visual acuity test 552 in accordance with an embodiment. Visual acuity test 552 is arranged at a distance X2 from a substantially first or right edge associated with vision system 326". When vehicle 101 is oriented with a first edge associated with vision system 326" that essentially faces visual acuity test 552, an image of visual acuity test 552 that is captured by vision system 326" may effectively be used to determine a visual acuity associated with a sensor of vision system 326" that is generally side-facing.

Distance X2 may be, in one embodiment, a distance from visual acuity test 552 to a first edge associated vision system 326" that effectively enables an individual (not shown) who is viewing visual acuity test 552 through a display screen of a teleoperations system (not shown) to see visual acuity test 552 as if he or she is viewing visual acuity test 552 from a predetermined distance associated with substantially perfect visual acuity, e.g., from approximately twenty feet away. Distance X2 may, however, vary depending upon factors including, but not limited to including, a size of optotypes on visual acuity test 552, a distance between an individual and a display screen, and/or a quality of the display screen.

Figure 6C:
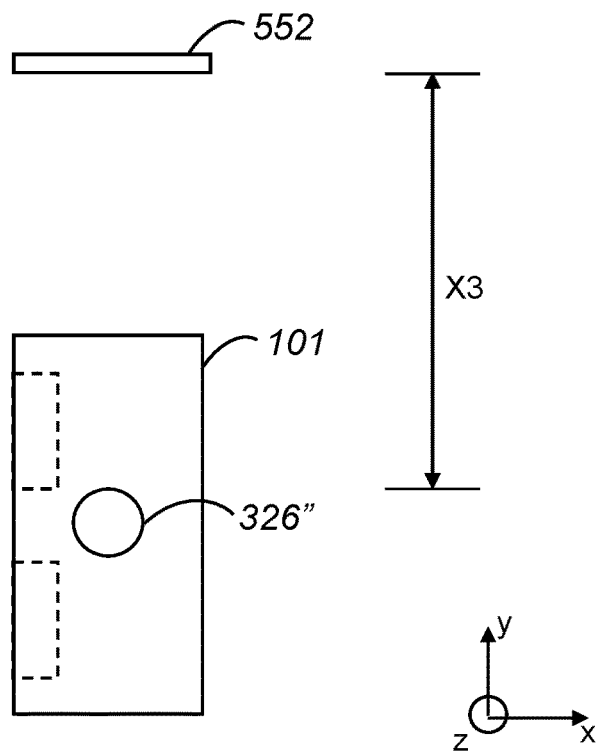
FIG. 6C is a diagrammatic representation of a vehicle in a third orientation with respect to an eye chart in accordance with an embodiment.

FIG. 6C shows vehicle 101 in a third orientation in which a back or rear side of vehicle 101 substantially faces visual acuity test 552 in accordance with an embodiment. Visual acuity test 552 is arranged at a distance X3 from a substantially back or rear edge associated with vision system 326". When vehicle 101 is oriented with a back edge associated with vision system 326" that essentially faces visual acuity test 552, an image of visual acuity test 552 that is captured by vision system 326" may effectively be used to determine a visual acuity associated with a sensor of vision system 326" that is generally back-facing.

Distance X3 may be, in one embodiment, a distance from visual acuity test 552 to a back edge associated vision system 326" that effectively enables an individual (not shown) who is viewing visual acuity test 552 through a display screen of a teleoperations system (not shown) to see visual acuity test 552 as if he or she is viewing visual acuity test 552 from a predetermined distance associated with substantially perfect visual acuity, e.g., from approximately twenty feet away. Distance X3 may, however, vary depending upon factors including, but not limited to including, a size of optotypes on visual acuity test 552, a distance between an individual and a display screen, and/or a quality of the display screen.

Figure 6D:
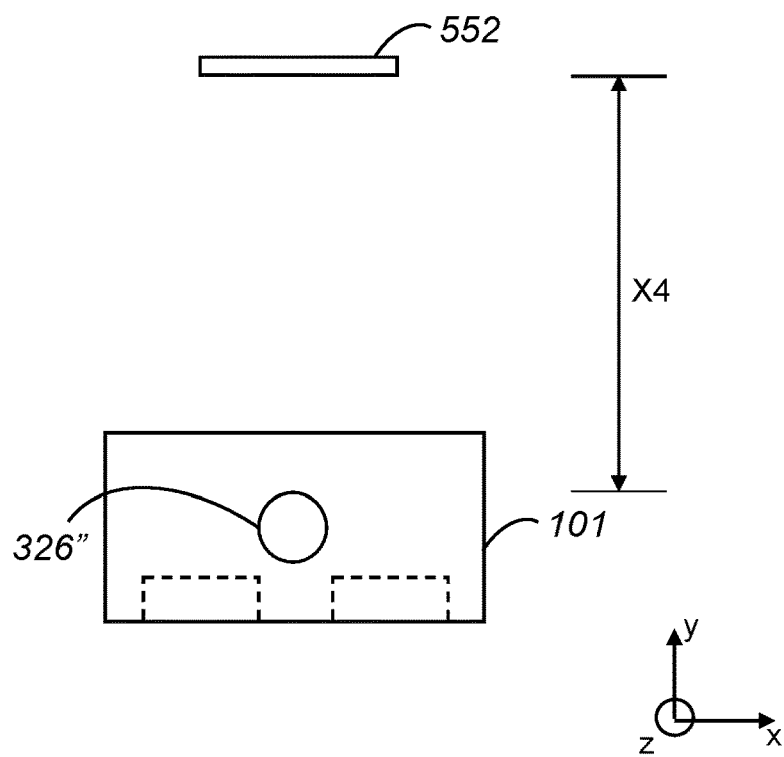
FIG. 6D is a diagrammatic representation of a vehicle in a fourth orientation with respect to an eye chart in accordance with an embodiment.

FIG. 6D is a representation of vehicle 101 in a fourth orientation in which a second or left side of vehicle 101 substantially faces visual acuity test 552 in accordance with an embodiment. Visual acuity test 552 is arranged at a distance X4 from a substantially second or left edge associated with vision system 326". When vehicle 101 is oriented with a second edge associated with vision system 326" that essentially faces visual acuity test 552, an image of visual acuity test 552 that is captured by vision system 326" may effectively be used to determine a visual acuity associated with a sensor of vision system 326" that is generally side-facing.

Distance X4 may be, in one embodiment, a distance from visual acuity test 552 to a first edge associated vision system 326" that effectively enables an individual (not shown) who is viewing visual acuity test 552 through a display screen of a teleoperations system (not shown) to see visual acuity test 552 as if he or she is viewing visual acuity test 552 from a predetermined distance associated with substantially perfect visual acuity, e.g., from approximately twenty feet away. Distance X4 may, however, vary depending upon factors including, but not limited to including, a size of optotypes on visual acuity test 552, a distance between an individual and a display screen, and/or a quality of the display screen.

It should be appreciated that distances X1, X2, X3, X4 may be approximately the same. In one embodiment, distances X1, X2, X3, X4 may each be approximately twenty feet. In another embodiment, distances X1, X2, X3, X4 may each be a particular distance which, when substantially added to a distance between a human and a screen on which visual acuity test 552 is displayed after being communicated from vehicle 101 to a display system, e.g., a display screen of a teleoperations system, is approximately twenty feet.

Figure 7:
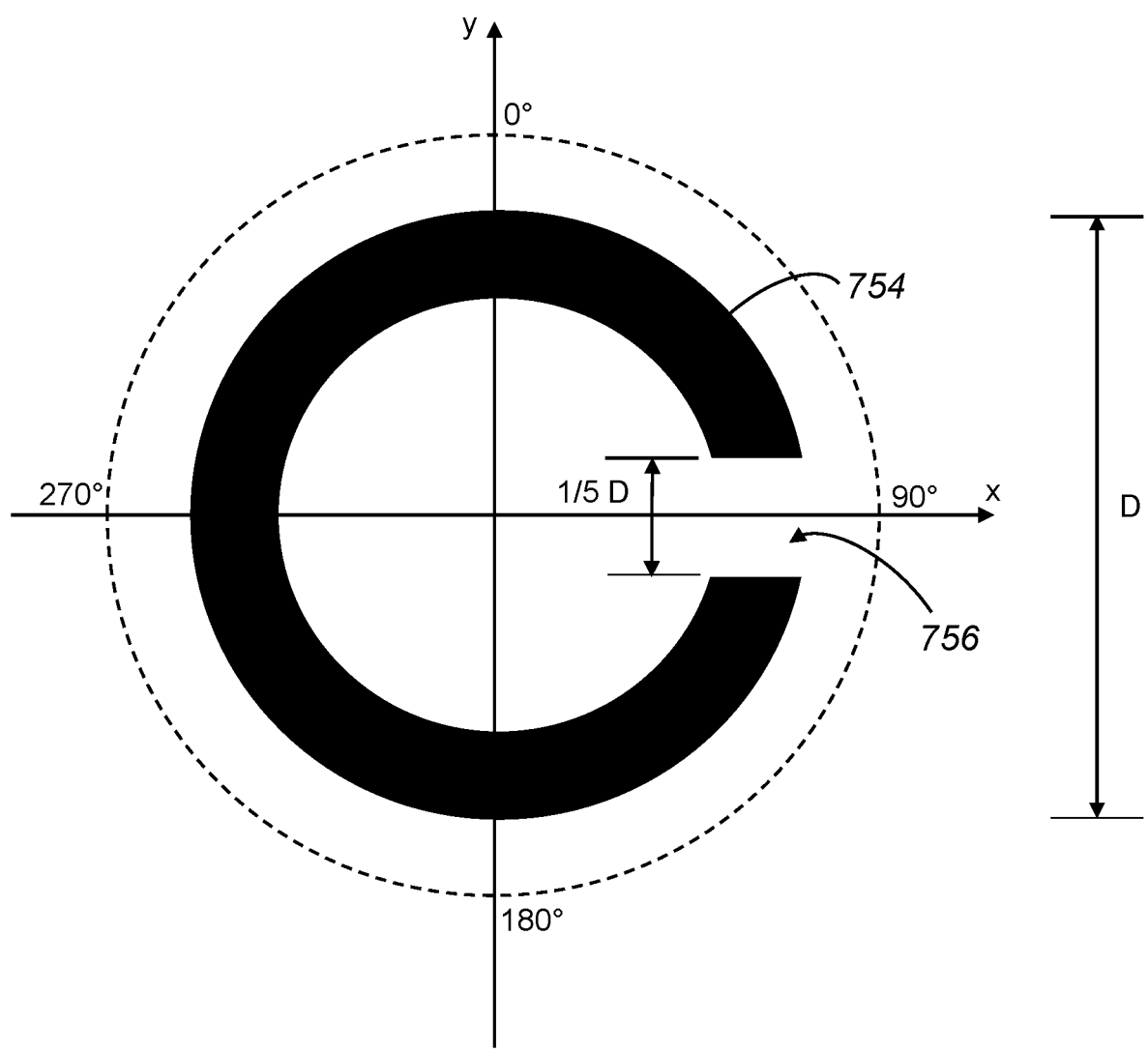
FIG. 7 is a diagrammatic representation of a Landolt C or ring in accordance with an embodiment.

The size of each Landolt C of a Landolt eye test chart may effectively be determined based on a distance at which a gap width in a Landolt C effectively subtends one minute of arc, or a distance at which an external diameter of a ring that forms a Landolt C effectively subtends five minutes of arc. FIG. 7 is a diagrammatic representation of a Landolt C or ring in accordance with an embodiment. A Landolt C or ring 754 generally has a circular perimeter, and includes a gap 756 in the perimeter. That is, Landolt C 754 is generally a ring with a break therein that is formed by gap 756. As shown, gap 756 is positioned at approximately 90 degrees along the perimeter or arc of Landolt C 754. However, it should be appreciated that gap 756 may generally be positioned substantially anywhere along the perimeter of Landolt C 754, as for example at approximately 180 degrees along the perimeter, at approximately 270 degrees along the perimeter, and at approximately zero degrees along the perimeter.

The dimensions of gap 756 may generally vary. For example, dimensions of gap 756 relative to an x-axis and/or a y-axis may vary. In one embodiment, a gap dimension such as a width may be a function of a width associated with Landolt C 754, That is, a gap size or dimension may vary with the size or dimension of Landolt C 754. For example, gap 756 may measure approximately one minute of the arc associated with Landolt C 754. A thickness of the perimeter of Landolt C 754 may be approximately one-fifth of a diameter (D) of Landolt C 754, and a width of gap 756 may also be approximately one-fifth of the diameter of Landolt C 754.

Figure 8A:
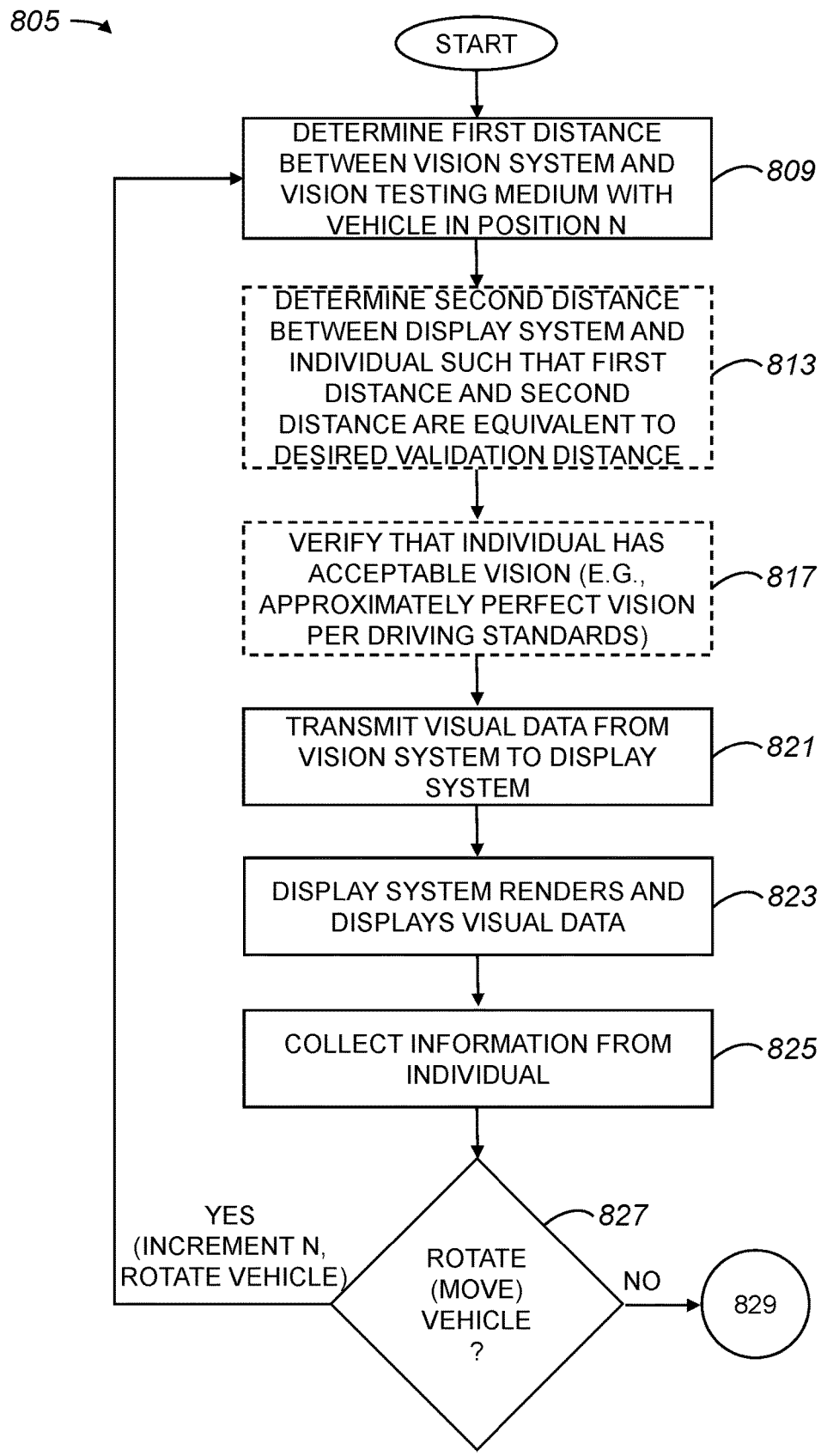
FIGS. 8A and 8B are a process flow diagram which illustrates a method of validating the visual acuity of a vision system in accordance with an embodiment.
Figure 8B:
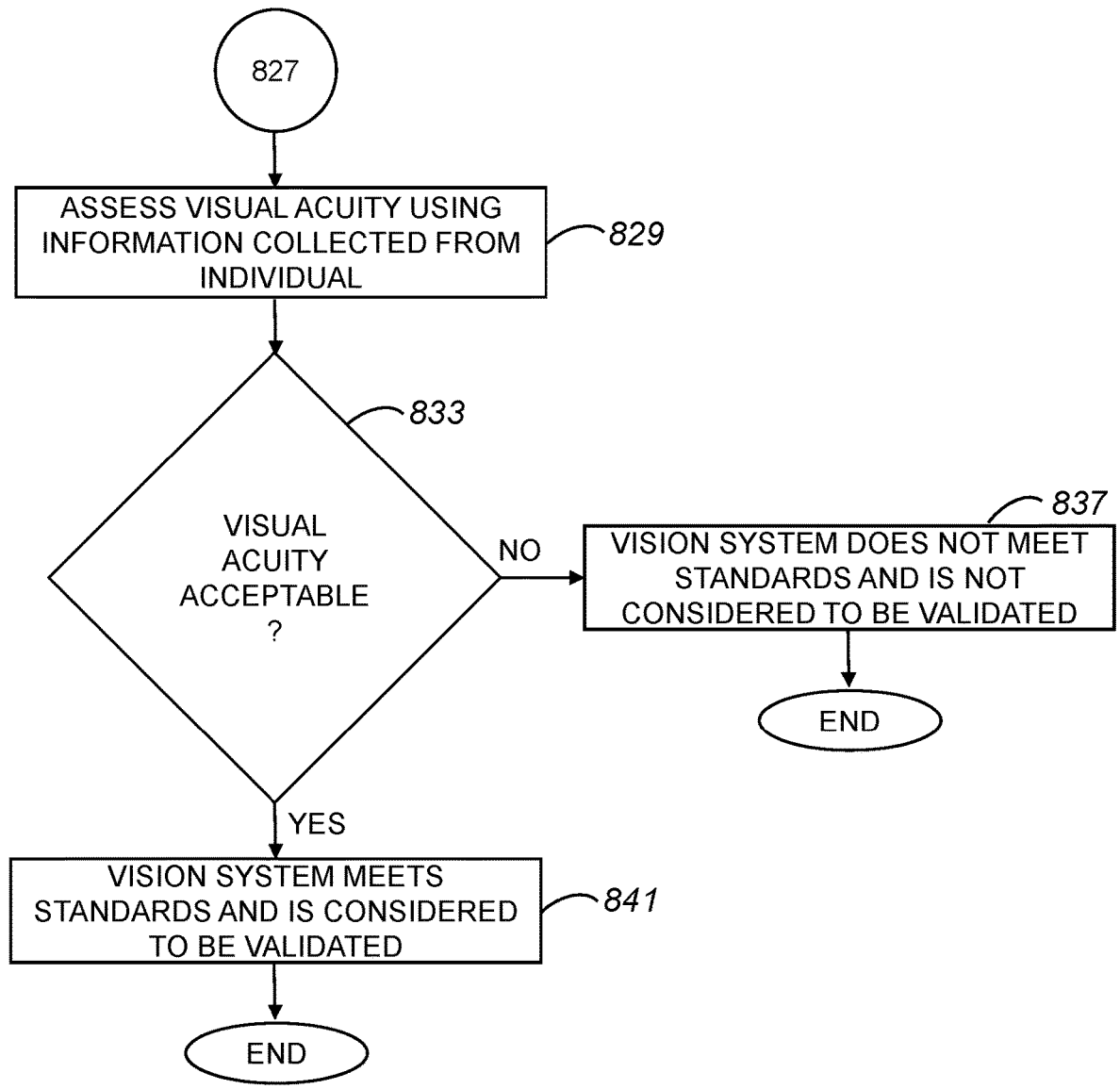

Referring next to FIGS. 8A and 8B, a method of validating the visual acuity of a vision system will be described in accordance with an embodiment. A method 805 of validating the visual acuity of a vision system of a vehicle begins at a step 809 in which a first distance between the vision system and a vision testing medium is determined when the vehicle is in a position N, e.g., a first position which may be a substantially front-facing position. Determining such a first distance may generally include, but is not limited to including, determining a distance that is consistent with a desired vision acuity validation distance, as will be discussed below. In one embodiment, the first distance may be a linear distance between a vision system mounted on an autonomous vehicle and an eye test chart such as a Landolt eye chart.

In an optional step 813, a second distance may be determined. The second distance is generally a distance between an individual and a display screen, e.g., a display screen of a teleoperations system, that is to be used in a validation process. The first distance and the second distance, together, may substantially define a desired vision acuity validation distance. In one embodiment, a desired vision acuity validation distance may be a function of the first distance and the second distance. For example, a first distance and a second distance may be selected such that a desired vision acuity validation distance, or an effective distance at which a human views a vision testing medium, is equivalent to approximately twenty feet. It should be appreciated that in some embodiments, a first distance may be approximately equal to the desired vision acuity validation distance. When the first distance is approximately equal to the desired vision acuity validation distance, optional step 813 may be substantially skipped.

From step 809 or an optional step 813, process flow proceeds to an optional step 817 in which it is verified whether an individual who is to participate in the validation process has acceptable vision or otherwise meets or exceeds minimum vision standards. Acceptable vision may be, for example, vision that is considered to be substantially adequate in view of standards or laws which specify a minimum visual acuity that is to be met by someone licensed to operate a motor vehicle. Acceptable vision may be defined to be associated with a level of visual acuity that meets or exceeds a particular threshold level. While acceptable vision may be defined in some jurisdictions as at least 20/40 or better in at least one eye, it should be appreciated that definitions of acceptable vision may vary widely. Verifying that the human has acceptable vision may include, but is not limited to including, subjecting the human to an eye test which may be a Landolt C test or any other suitable step. Step 817 is generally optional, as an individual with a valid driver's license will typically have met vision standards for operating a motor vehicle.

In a step 821, the vision system gathers visual or image data, and transmits the visual data to a display system which may be viewed by an individual. Transmitting the visual data may include providing or sending the visual data through a network to the display system. The network may be any suitable wireless and/or wireless network. For example, the network may be a 3G/4G/5G network, an LTE network, and/or a Wi-Fi network.

Once the display system obtains the visual data, the visual data is rendered and displayed on the display system in a step 823. Displaying the visual data generally includes displaying a rendering of the vision testing medium. In one embodiment, displaying the visual data includes displaying a captured image of a Landolt eye chart on a display system of a teleoperations system.

Information relating to the displayed visual data is collected from an individual in a step 825. That is, information pertaining to how the individual perceives the displayed visual data is obtained. It should be appreciated that any suitable method may be used to collected information from an individual. By way of example, the individual may be asked to use a user interface to enter what he or she sees in the visual data into a computer application running on a computing system, or the individual may speak what he or she sees into a recording system or to another human who notes what the individual speaks.

After information is collected from an individual, it is determined in a step 827 whether the vehicle is to be rotated or otherwise moved relative to the vision testing medium. In other words, if is determined if the vision system of the vehicle is to be further evaluated, e.g., whether other sensors of the vision system such as sensors that face a different direction are to be further evaluated.

If the determination in step 827 is that the vehicle is to be rotated or otherwise moved relative to the vision testing medium, position N is incremented and the vehicle is rotated, and process flow returns to step 809 in which a first distance between a vision system and a vision testing medium are determined with the vehicle in position N. On the other hand, if the determination is that the vehicle is not to be rotated or otherwise moved, the implication is that sufficient information has been collected, e.g., substantially every sensor associated with vision system has been evaluated. Accordingly, process flow moves from step 827 to a step 829 in which visual acuity is assessed using information collected from the individual. One method of assessing the visual acuity of the human using collected information will be discussed below with respect to FIG. 9.

From step 829, process flow proceeds to a step 833 in which it is determined whether the visual acuity is acceptable. Such a determination may include determining whether the visual acuity of the individual, as assessed in step 829, indicates that at least minimum standards have been met and/or that a threshold level has been met or exceeded. If the determination is that the visual acuity is not acceptable, then the vision system is identified as not meeting standards, and is not considered to be validated in a step 837. The method of validating the visual acuity of a vision system is terminated upon identifying the vision system as not validated.

Alternatively, if the determination in step 833 is that the visual acuity is acceptable, the implication is that individual has met at least minimum standards through the use of the vision system. As such, the vision system may be considered to be capable of providing images to a teleoperator that have at least an adequate level of clearness and sharpness. Accordingly, process flow moves from step 833 to a step 841 in which the vision system is identified as meeting standards, and is considered to be validated. The method of validating the visual acuity of a vision system is completed upon identifying the vision system as validated.

Figure 9:
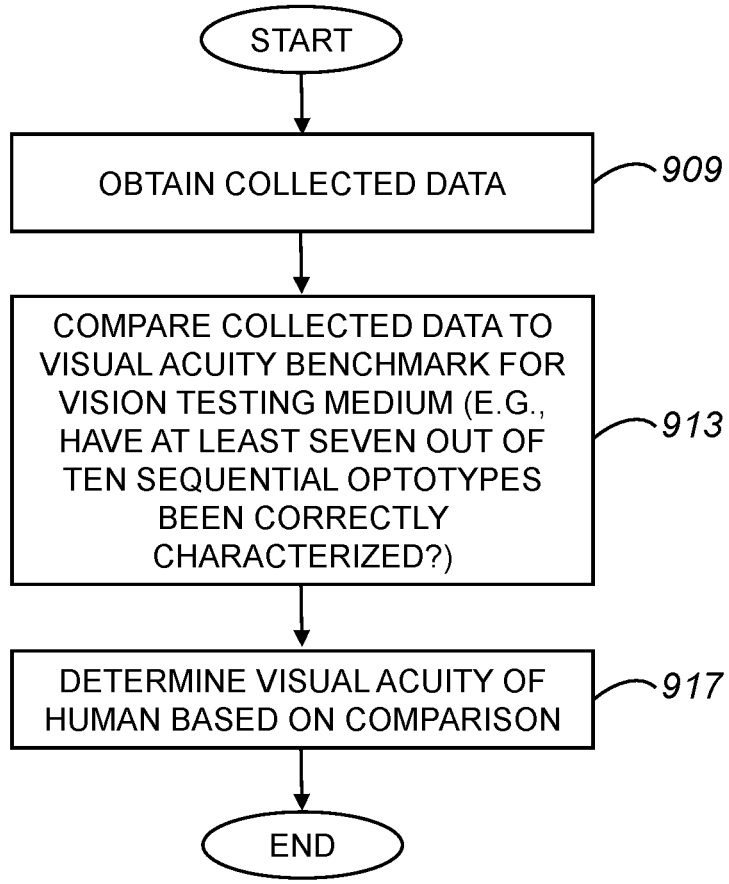
FIG. 9 is a process flow diagram which illustrates a method of assessing visual acuity, e.g., step 829 of FIG. 8A, in accordance with an embodiment.

FIG. 9 is a process flow diagram which illustrates a method of assessing visual acuity, e.g., step 829 of FIG. 8A, in accordance with an embodiment. Method 829 of assessing visual acuity begins at a step 809 in which the data collected in step 825 of FIG. 8A is obtained by an assessment system. Such an assessment system may be an application that runs on a computing system or at least one server.

The collected data is compared to a visual acuity benchmark for the vison testing medium in a step 913. The visual acuity benchmark may include information that indicates what collected data is expected to indicate if the collected data meets at least minimum visual acuity standards. By way of example, if a vision testing medium is a Landolt eye chart, a visual acuity benchmark may include an indication of which Landolt C's of the Landolt eye chart an individual may be able to accurately read if at least a minimum visual acuity standard is to be considered to be met. Further, a percentage of correctly identified optotypes, e.g., Landolt C's, with respect to a particular number of optotypes may be specified as a visual acuity benchmark, e.g., identifying approximately seventy percent or at least approximately seven out of ten optotypes correctly may be specified as a benchmark for a substantially minimum acceptable visual acuity.

Based on the comparison of data, the visual acuity of the individual is determined in a step 917. Such a determination may generally specify whether the individual meets at least minimum visual acuity standards. In one embodiment, if the individual is determined to meet at least minimum visual acuity standards, a vision system may be considered to also meet at least minimum visual acuity standards. After the visual acuity of the human is determined, the process of assessing visual acuity is completed.

Figure 10:
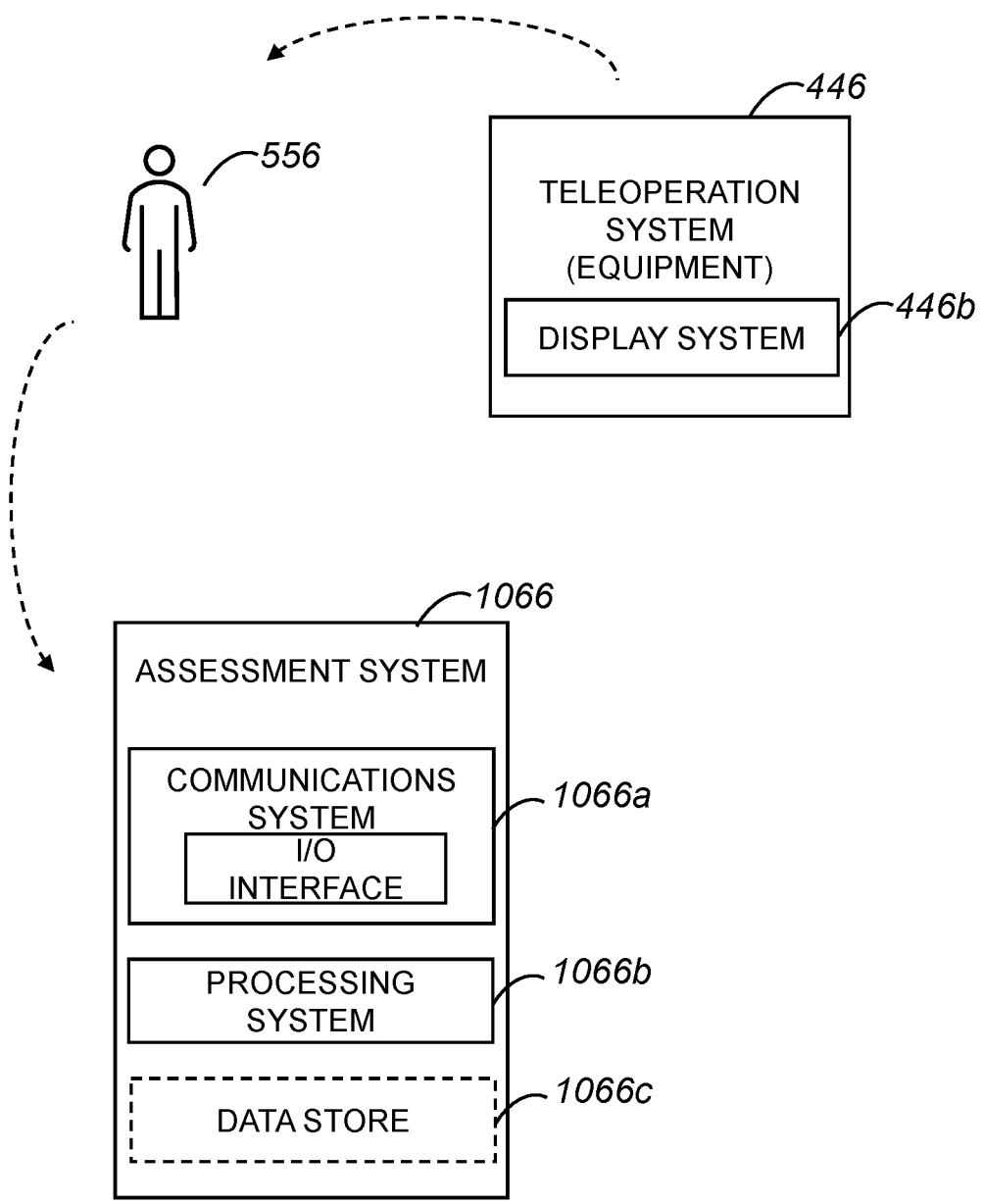
FIG. 10 is a diagrammatic representation of a system which may be used to assess visual acuity in accordance with an embodiment.

As mentioned above, the visual acuity of a human may be assessed, and the assessment of the visual acuity of the human may be used to effectively validate a vision system of an autonomous vehicle. FIG. 10 is a diagrammatic representation of a system which may be used to assess visual acuity of a human using a teleoperations system in accordance with an embodiment. Human or individual 556 may view an image on a display system, e.g., a display screen included in display system 446b of teleoperation system 446. An assessment system 866 is arranged to collect or to otherwise obtain data from individual 556 that relates to what individual 556 sees displayed on display system 446b. For example, if display system 446b displays an eye test chart such as a Landolt eye chart, then assessment system 866 may collect information relating to how accurately individual 556 sees a gap in each Landolt C on the Landolt eye chart.

Assessment system 1066 generally includes a communications system 1066a, a processing system 1066b, and an optional data store 1066c. Communications system 1066a, which may include an input/output (I/O) interface, is generally arranged to obtain data from individual 556. Communications system 1066a may be arranged to communicate with individual 556 over a network, e.g., with a device such as a smartphone (not shown) used by individual 556 to transmit information to assessment system 1066, and may be arranged to generally communicate with other nodes of a network, e.g., with a database on which data such as visual acuity data is stored.

The I/O interface of communications system 1066a may vary widely. The I/O interface may be configured as a graphical user interface into which individual 556, or another person, may enter data relating to what her or she is able to clearly and sharply discern from an image displayed on display system 446. The I/O interface may instead, or additionally, be configured to receive audio and/or visual information that is collected from individual 556 as individual 556 speaks and/or gestures, e.g., verbalizes and/or gestures to indicate whether a Landolt C has a gap facing up, down, right, or left. It should be appreciated that data collected from individual 556 may be obtained indirectly from individual 556, as for example from a database into which the data has been entered.

Processing system 1066b is arranged to process data collected from individual 556 using communications system 866a to assess the visual acuity of individual 556. In one embodiment, the collected data may be compared with benchmark data stored in optional data store 1066c. In another embodiment, the collected data may be compared with benchmark data obtained from a network using communications system 1066a. Processing the data includes, but is not limited to including, assessing the data to determine whether the data indicates that individual 556, when viewing an image displayed on display system 446b, meets at least a minimum standard for visual acuity. When the data indicates that at least a minimum standard for visual acuity is achieved, a vision system such as vision system 326 of FIG. 3 that provides the viewed image may be substantially classified as meeting at least the minimum standard for visual acuity.

Factors used to determine whether individual 556 and, hence, a vision system such as vision system 326 of FIG. 3, may generally vary widely. In one embodiment, individual 556 may be identified as meeting at least a minimum standard for visual acuity if he or she is able to correctly identify at least a predetermined number of optotypes such as a Landolt C out of a particular number of optotypes. example, if individual 556 is able to identify at least seven Landolt C characters out of ten Landolt C characters, individual 556 and, hence, a vision system such as vision system 326 of FIG. 3 may be substantially identified as meeting at least a minimum standard for visual acuity. It should be appreciated that different sensors within a vision system may effectively be evaluated to determine the visual acuity associated with each sensor.

A visual acuity assessment which utilizes an eye chart such as a Landolt C eye chart is not limited to being associated with a teleoperation system. That is, a visual acuity assessment may effectively be leveraged for use with systems other than teleoperation systems. By way of example, a visual acuity assessment may be performed to calibrate a simulation system configured to facilitate the training to teleoperation operators. In other words, the visual acuity of a simulation system may be assessed such that the overall performance of a system which allows for the simulation of driving environments may be evaluated. Assessing the visual acuity may be associated with substantially verify visual realism. It should be understood that a simulation system may be used to validate safety, e.g., end-to-end safety, of a teleoperations system.

Figure 11:
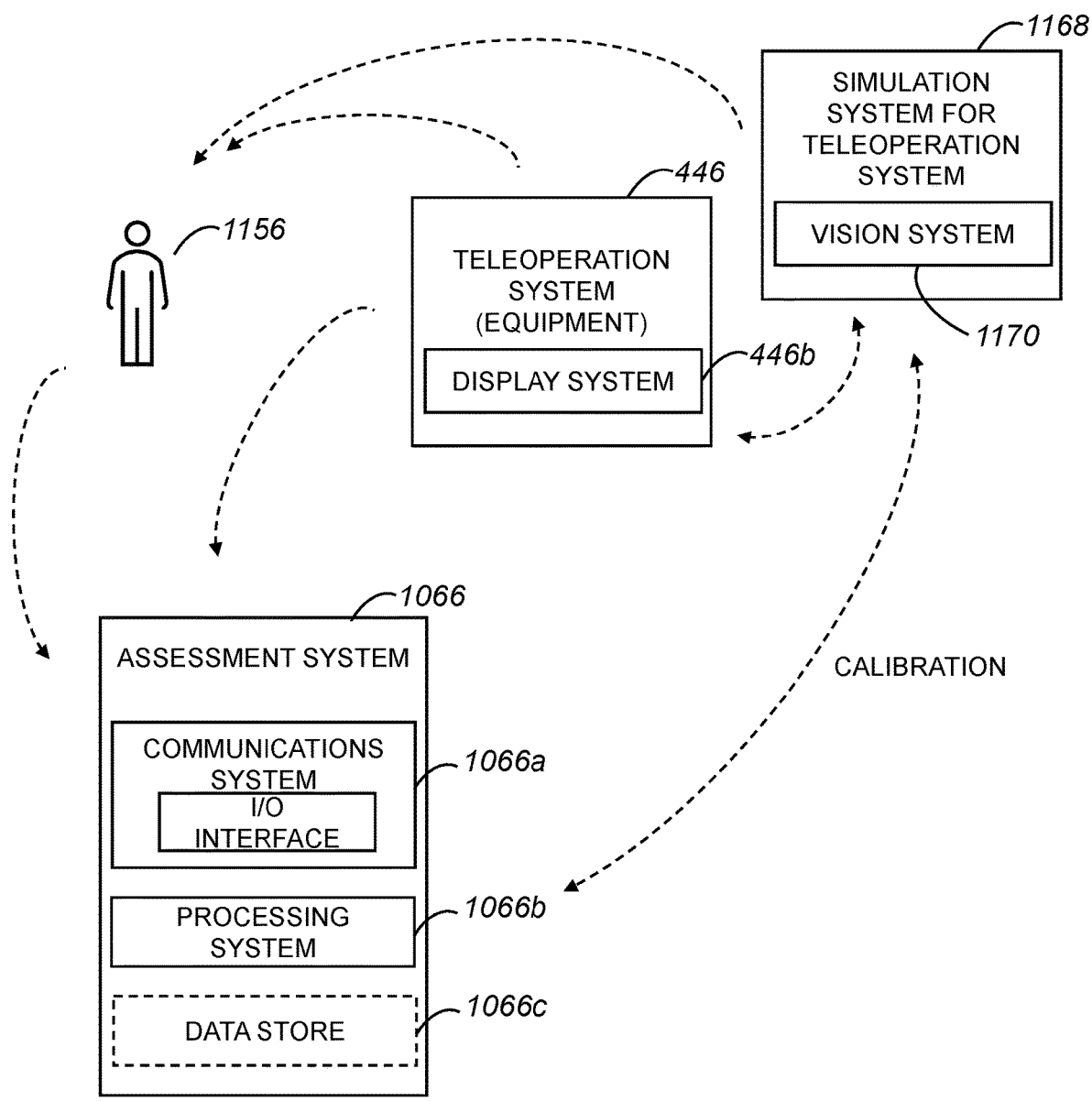
FIG. 11 is a diagrammatic representation of a system which may be used to assess visual acuity of a teleoperations system and a simulation system in accordance with an embodiment.

FIG. 11 is a diagrammatic representation of a system which may be used to assess visual acuity of a teleoperations system and a simulation system in accordance with an embodiment. A human or individual 1156 may view an image on a display system, e.g., a display screen associated with a vison system 1170 of a simulation system 1168. The image may be part of a recorded video. Individual 1156 may also view an image, e.g., a substantially live video image, on display system 446b of teleoperation system 446. In one embodiment, vison system 1170 may cause an image to be displayed on a display screen of display system, 446b. It should be appreciated that an image rendered by display system 446b and an image rendered by vision system 1170 may be viewed by individual 1156 at different times.

Simulation system 1168 may include hardware and/or software which allows actual driving on roads to be substantially simulated. For example, video obtained by sensors or an autonomous vehicle may be recorded and rendered within simulation system 1168 such that individual 1156 may view the video when the video is rendered by vision system 1170, although it should be appreciated that a video may instead be substantially fully synthetic, e.g., effectively generated without real-world sensor data or video. The video rendered by vision system 1170 may be displayed to individual 1156, as for example on display screen 446b or a separate display screen associated with simulation system 116. In one embodiment, vision system 1170 may provide a rendering of an eye test chart such as a Landolt eye chart that individual 1156 may view.

An assessment system 1066 is arranged to collect or to otherwise obtain data from individual 1156 that relates to what individual 1156 sees displayed on display system 446b. For example, if display system 446b displays an eye test chart such as a Landolt eye chart, then assessment system 1066 may collect information relating to how accurately individual 1156 sees a gap in each Landolt C on the Landolt eye chart. Further, if vision system 1170 provides a rendering of a Landolt eye chart that is displayed to individual 1156, assessment system 1066 may collect information relating to how accurately individual 1156 sees a gap in each Landolt C on the Landolt eye chart.

Assessment system 1066 includes communications system 1066a, processing system 1066b, and optional data store 1066c. Assessment system 1066 may be remote with respect to teleoperation system 446 and simulation system 1168, although it should be appreciated that assessment system 1066 may be local with respect to either or both teleoperation system 446 and simulation system 1168.

Communications system 1066a, which may include an input/output I/O interface, is generally arranged to obtain data from individual 1156. Communications system 1066a may be arranged to communicate with individual 1156 over a network, e.g., with a device such as a smartphone (not shown) used by individual 556 to transmit information to assessment system 1066, and may be arranged to generally communicate with other nodes of a network, e.g., with a database on which data such as visual acuity data is stored. Alternatively, communication system 1066a may communicate with individual 1156 through teleoperation system 446 and/or simulation system 1168.

Processing system 1066b is arranged to process data collected from individual 1156 using communications system 1066a to assess the visual acuity of individual 1156 with respect to what individual 1156 sees with respect to display system 446b and/or vision system 1170. In one embodiment, the collected data may be compared with benchmark data stored in optional data store 1066c. In another embodiment, the collected data may be compared with benchmark data obtained from a network using communications system 1066a. It should be appreciated that data obtained from user with respect to display system 446b may effectively be used as benchmark data for comparison purposes when data is obtained with respect to vision system 1170. Processing the data includes, but is not limited to including, assessing the data to determine whether the data indicates that individual 1156, when viewing an image displayed on display system 446b, meets at least a minimum standard for visual acuity. When the data indicates that at least a minimum standard for visual acuity is achieved, a vision system such as vision system 326 of FIG. 3 that provides the viewed image may be substantially classified as meeting at least the minimum standard for visual acuity.

Once vision system 326 is classified as meeting at least a minimum standard for visual acuity, data obtained from individual 1156 when individual 1156 views an image rendered by vision system 1170 may be processed to ascertain whether vision system 1170 meets visual acuity standards, e.g., at least a minimum standard for visual acuity of a simulation system. Such an assessment may include, but is not limited to including, determining whether individual 1156 views an eye chart rendered by display system 446 with approximately the same visual acuity with which individual 1156 views an eye chart rendered by vision system 1170. For example, simulation system 1168 may be identified as substantially calibrated and as meeting visual acuity standards when the visual acuity associated with simulation system 1168 is approximately same as the visual acuity associated with teleoperations system 446.

Figure 12:
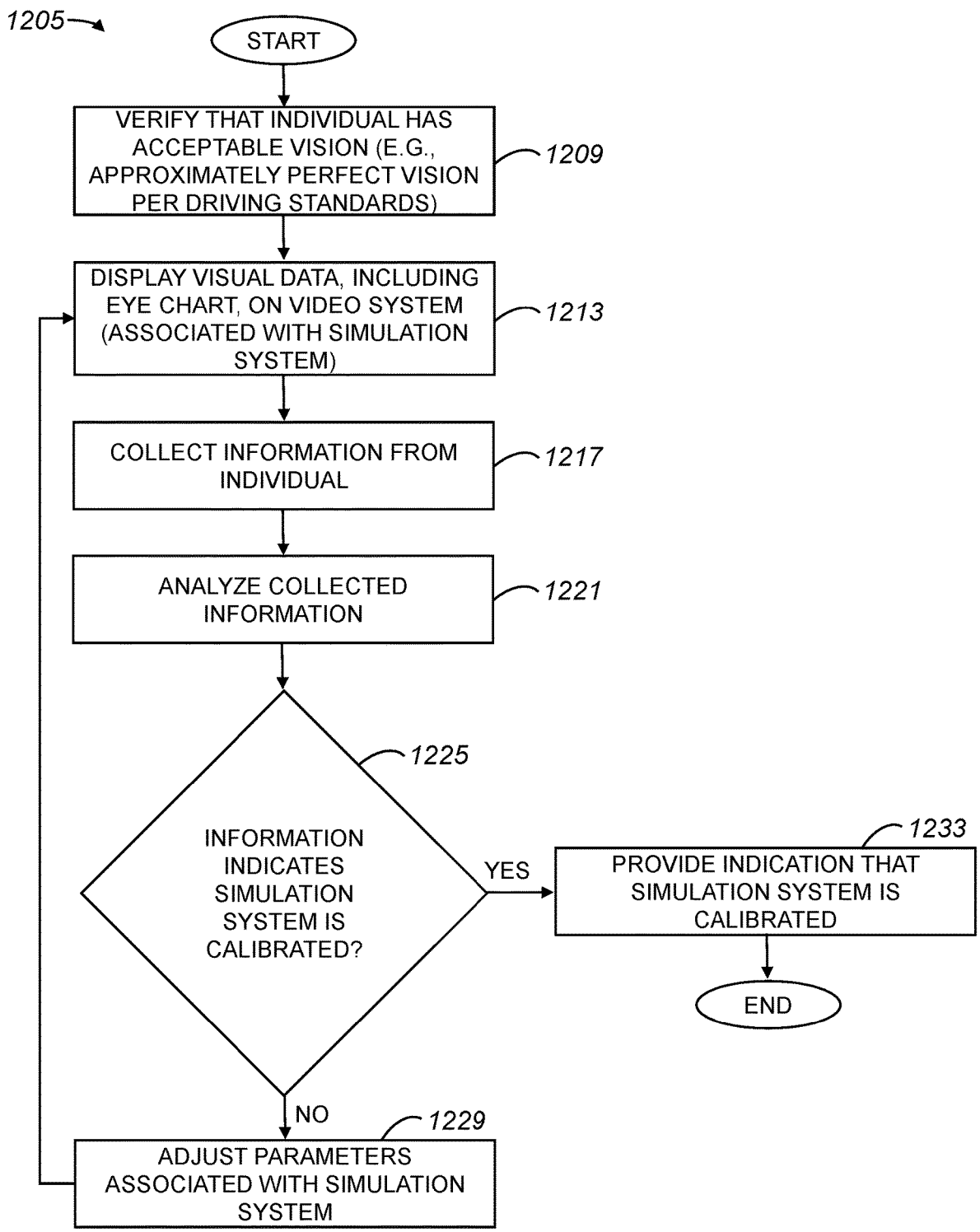
FIG. 12 is a process flow diagram which illustrates a method of calibrating a simulation system for autonomous vehicles that includes an assessment of visual acuity in accordance with an embodiment.

With reference to FIG. 12, a method of calibrating a simulation system for use in enabling an individual to simulate driving a vehicle in real conditions that includes an assessment of visual acuity in accordance with an embodiment. A method 1205 of calibrating a simulation system begins at a step 1209 in which it is verified that an individual has vision that is within a range of acceptable visions. The simulation system may generally be a system that enables driving to be simulated, e.g., a system that allows a teleoperation system to be used to enable an operator to practice driving using a simulated scene or a video recording of an actual scene.

In a step 1213, visual data, including an eye chart such as a Landolt eye chart, is rendered on a video system. The video system may be part or, or may be in communication with, a simulation system. Rendering the visual data on a video system may include, but is not limited to including, displaying the visual data on a display screen. The visual data may be viewed or otherwise seen by an individual, and information relating to the visual data may be collected from the individual in a step 1217. The visual data may be collected using any suitable method including, but not limited to including, the individual inputting the data into an assessment system, the individual verbalizing what he or she sees and providing the information to an assessment system, and/or the individual providing an indication or what he or she sees directly or indirectly to an assessment system.

After information is collected from the individual, the collected information is analyzed in a step 1221. Analyzing the collected information may include comparing the collected information with data to determine whether the collected information indicates that the simulation system is properly calibrated. One method of analyzing collected information will be discussed below with reference to FIG. 13.

From step 1221, process flow moves to a step 1225 in which it is determined whether the collected information indicates that the simulation system is calibrated. That is, it is determined whether the visual acuity indicated by the information is at an acceptable level. If the determination is that the simulation system is calibrated, then in a step 1233, an indication that the simulation system is calibrated is provided, and the method of calibrating a simulation system is completed.

Alternatively, if it is determined in step 1225 that the information does not indicate that the simulation system is calibrated, the implication is that parameters associated with the simulation system may need to be adjusted or otherwise tuned. Accordingly, in a step 1229, parameters associated with the simulation system are adjusted to effectively calibrate the simulation system. Parameters that may be adjusted may include, but are not limited to including, anti-aliasing parameters, color correction parameters, visual resolution parameters, lighting parameters, and/or the like. In one embodiment, adjusting parameters associated with a simulation system may involve identifying parameters associated with a teleoperations system and effectively matching the parameters of the simulation system with the parameters of the teleoperations system. Once parameters are adjusted, process flow returns to step 1213 in which visual data is displayed on the video system.

Figure 13:
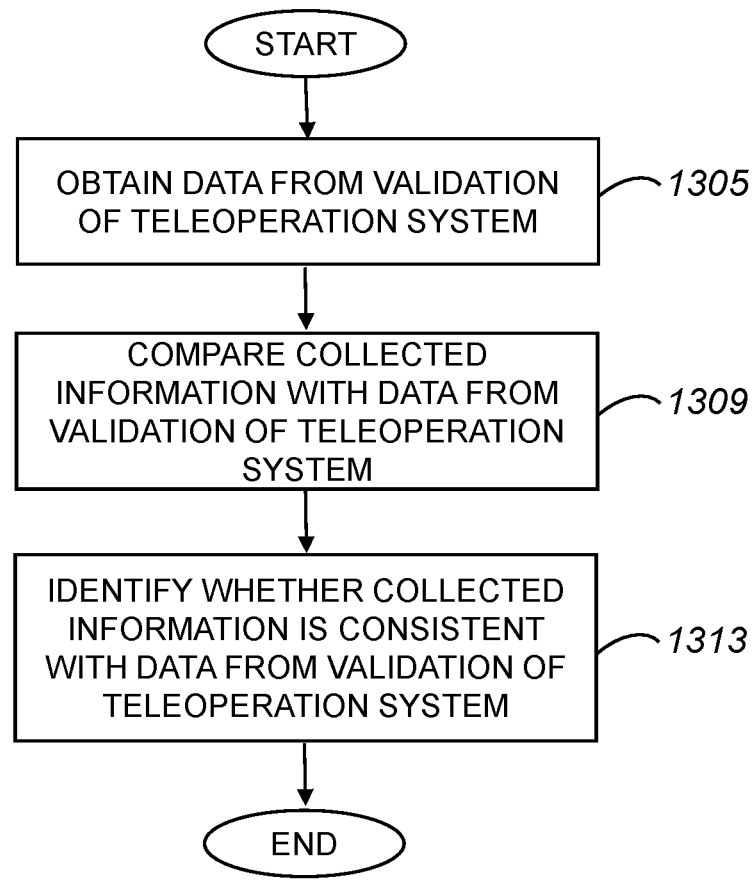
FIG. 13 is a process flow diagram which illustrates a method of analyzing collected information associated with a simulation system, e.g., step 1221 of FIG. 12, in accordance with an embodiment.

With reference to FIG. 13, one method of analyzing collected information associated with a simulation system, e.g., step 1221 of FIG. 12, will be described in accordance with an embodiment. Method 1221 of analyzing collected information begins at a step 1305 in which data associated with the validation of a teleoperation system is obtained, e.g., from a data store such as data store 1066c of FIGS. 10 and 11. The data may be associated with the same individual who provided the collected information. In other words, the collected information may be collected from the same individual who was effectively used to validate the teleoperation system.

The collected information is compared with the data from the validation of the teleoperation system in step 1309. Then, in a step 1313, it is identified whether the collected information is consistent with the data from the validation of the teleoperation system. That is, it is determined whether the visual acuity or quality associated with the simulation system is similar to, or otherwise approximately the same as, the visual acuity or quality associated with the teleoperation system. In one embodiment, determining whether the collected information is consistent with the data from the validation of the teleoperation system includes determining whether a visual acuity associated with the teleoperations system. In another embodiment, determining whether the collected information is consistent with the data from the validation of the teleoperation system may involve determining whether the collected information indicates an acceptable level of visual acuity. For example, if the collected information indicates the ability to view an eye chart at approximately a 20/200 vision level, the implication may be that the collected information is consistent with the data from the validation of the teleoperation system. Upon identifying whether the collected information is consistent with the data from the validation of the teleoperation system, the method of analyzing collected information is completed.

Figure 14:
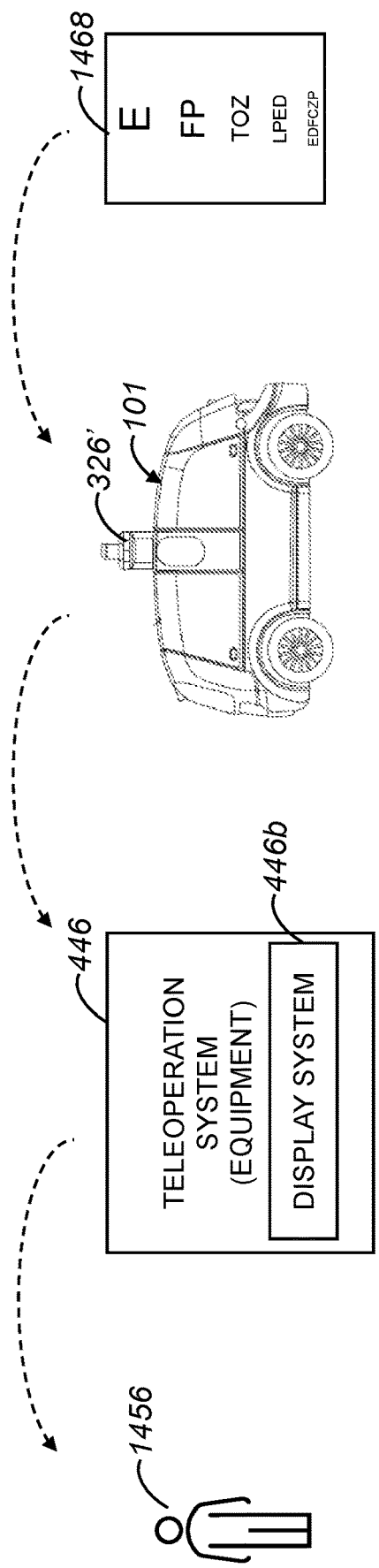
FIG. 14 is a diagrammatic representation of a system which facilitates the validation of a vision system of a vehicle using a Snellen eye chart and a human in accordance with an embodiment.

While the use of a Landolt C eye chart has been described as being used to assess visual acuity, it should be understood that the use of eye charts is not limited to a Landolt C eye chart. For example, a Snellen eye chart may be used in some instance. FIG. 14 is a diagrammatic representation of a system which facilitates the validation of a vision system of a vehicle using a Snellen eye chart and a human in accordance with an embodiment. A vision test medium 1468, which may be a Snellen eye test chart may be positioned within range of vision system 326' of autonomous vehicle 101. Vision system 326' may provide an image of Snellen eye chart 1368 to display system 446b of teleoperations system 446, and a human 1456 may view the image to determine how clearly and sharply he or she is able to see the image, or at least the portion of the image which depicts Snellen eye chart 1468. If human 1456 is able to clearly and sharply discern Snellen eye chart 1468, e.g., read lines of optotype such as letters on Snellen eye chart 1468, when viewed on display system 446b, then vision system 326' may effectively be validated.

Figure 15:
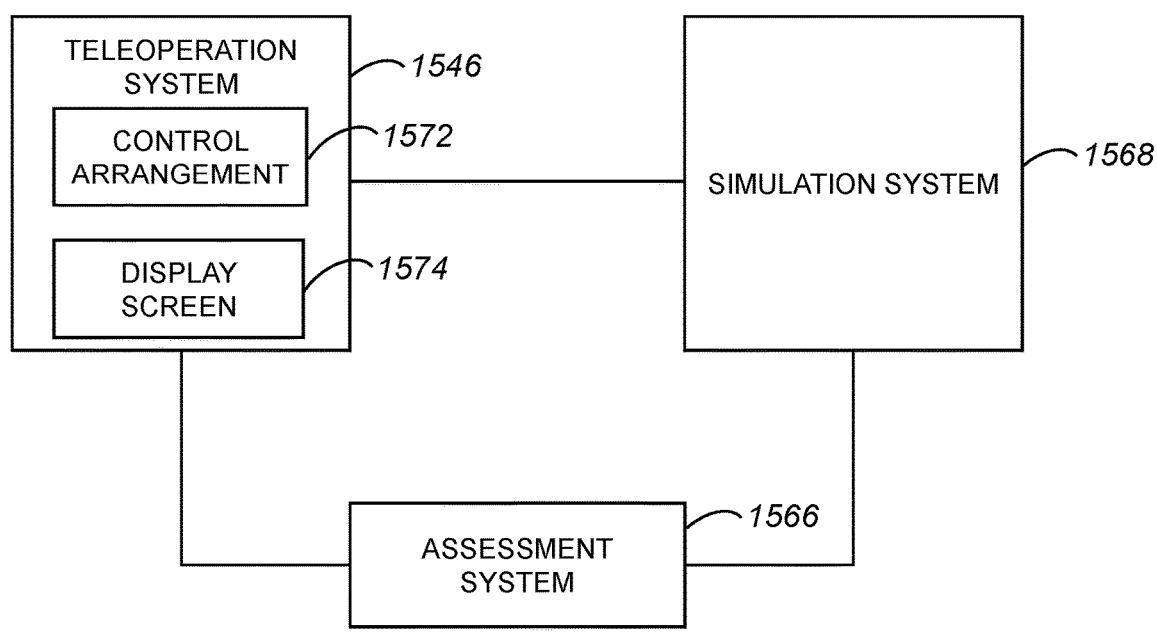
FIG. 15 is a block diagram representation of an overall system which includes a teleoperation system, a simulation system, and an assessment system in accordance with an embodiment.

Referring next to FIG. 15, an overall system arranged to evaluate the visual acuity or quality associated with a teleoperation system and a simulation system will be described in accordance with an embodiment. An overall system 1570 includes a teleoperation system 1546, a simulation system 1568, and an assessment system 1566. Teleoperation system 1546 includes a control arrangement 1572, which is generally configured to enable a vehicle or a robotic apparatus to be controlled, and a display screen 1574. Control arrangement 1572 may include, but is not limited to including, a steering wheel or apparatus, speed control components, a gear shift, and a communication system. Display screen 1574 may be part of a display system, and may be a monitor arranged to display the environment around a vehicle or robotic apparatus that may be remotely controlled using teleoperations system 1546.

Simulation system 1568 includes hardware and/or software configured to provide a simulated environment that may be used, as for example by teleoperation system 1546, to essentially practice driving. The simulated environment may include, but is not limited to including, images such as video images of real environments through which a vehicle or robotic apparatus may be driven. In one embodiment, a visual rendering of an environment may be provided by simulation system 1568 to display screen 1574 such that control arrangement 1572 may be used to effectively simulate driving in the environment. That is, control arrangement 1572 may be configured to enable teleoperation system 1546 to be used to simulate driving in an environment provided by simulation system 1568.

Assessment system 1566 is configured to obtain data associated with teleoperation system 1546 and data associated with simulation system 1568 to assess the visual acuity of teleoperation system 1546 and/or simulation system 1568, Using the data, assessment system 1566 may determine whether visual acuity standards or expectations are met. In one embodiment, assessment system 1566 may determine whether the visual acuity associated teleoperation system 1546 and the visual acuity associated with simulation system 1568 are consistent with each other, e.g., are approximately the same.

Although only a few embodiments have been described in this disclosure, it should be understood that the disclosure may be embodied in many other specific forms without departing from the spirit or the scope of the present disclosure. By way of example, a vision system may be independently tested using the methods mentioned above. That is, the visual acuity of a vision system may be tested and, hence, validated even when the vision system is not installed on an autonomous vehicle. By testing visual acuity of a vision system before the vision system is installed on an autonomous vehicle, adjustments may be made to the vision system that may be more readily made. In one embodiment, the visual acuity may be tested using a display system that is separate from a teleoperation system.

A Landolt C circle or ring has generally been described as including a gap that is positioned along a perimeter of the ring. While the gap has been described as being positioned either at approximately zero degrees, approximately 90 degrees, approximately 180 degrees, or approximately 270 degrees along the ring, it should be appreciated that the gap may generally be positioned substantially anywhere along the ring. For instance, the gap may be positioned at approximately 45 degrees, approximately 135 degrees, approximately 225 degrees, or approximately 315 degrees along the ring.

While visual acuity standards have generally been specified in terms of what an average person may see on a vision eye chart when he or she is positioned at a predetermined distance away from the vision eye chart, it should be appreciated that other visual acuity standards may be implemented. In addition, visual acuity tests and/or vision test mediums are not limited to being used to facilitate a determination what a human, e.g., a teleoperator, is able to clearly see from a predetermined distance.

Visual acuity standards may generally involve determining whether an individual with substantially "perfect" vision is able to see a vision eye chart from a particular distance. Substantially perfect vision may be defined, for example, as approximately 20/20 vision in which an individual may clearly see and accurately read an eye chart from approximately twenty feet away or approximately 6/6 vision in which an individual may clearly see and accurately read an eye chart from approximately six meters away. It should be appreciated that the definition of perfect vision may vary widely, and that in some situations, an individual with less than approximately 20/20 vision, e.g., an individual with 20/40 vision, may be identified as having substantially perfect or otherwise acceptable vision.

In general, when a vision system of an autonomous vehicle is determined not to pass a visual acuity test, adjustments may be made to the vision system, and further visual acuity assessments may be made to determine if the vision system may eventually successfully pass a visual acuity test. Adjustments may include, but are not limited to including, altering native camera resolutions for cameras in the vision system, altering circuitry onboard the autonomous vehicle to reduce any degradation in resolution, installing new cameras in the vision system, substantially optimizing the parameters associated with video processing algorithms to provide improved image output, increasing bandwidth allocations, and/or changing the field of view associated with the vision system to focus more on a region of interest.

For example, if a vision system of an autonomous vehicle is determined not to pass a visual acuity test, if image processing onboard the vehicle is identified as contributing to a degradation of resolution, adjustments may be made to algorithms, bandwidth allocations, cameras, etc. to improve the resolution.

As previously mentioned, different sensors within a vision system may effectively be evaluated to determine the visual acuity associated with each sensor. In one embodiment, the visual acuities associated with multiple sensors in a vision system may be evaluated such that the vision system, overall, may be considered to provide adequate visual acuity for teleoperations substantially only when each of the multiple sensors individual provides at least a minimum acceptable level of visual acuity. It should be appreciated, however, that as some sensors of a vision system may be considered to be more critical than others, when the visual acuities associated with the more critical sensors are substantially all considered to meet at least a minimum acceptable level of visual acuity, then the vision system may be considered to provide at least a minimum acceptable level of visual acuity.

An individual has been described as being a part of an overall system which allows for visual acuity of a display system of a teleoperation system to be assessed and/or for visual acuity of a vision system of a simulation system to be assessed. In one embodiment, in lieu of an individual, mechanisms may instead be used to assess visual acuity of a display system and/or a vision system. Such mechanisms may scan an eye chart that is rendered on display screen, and attempt to identify optotypes on the eye chart. The accuracy with which the optotypes are obtained and identified by a mechanism, e.g., a scanner or scanning device, may be used to determine visual acuity.

The calibration of a simulation system, as described above with respect to FIG. 12, may be a continual process. For example, even in the event that an acceptable level of calibration with a current set of views from a camera is achieved, a change of camera views may result in a need to substantially re-calibrate the simulation system. Such a change in camera views may include, but is not limited to including, changing from a substantially standard camera view to a panoramic camera view.

An autonomous vehicle has generally been described as a land vehicle, or a vehicle that is arranged to be propelled or conveyed on land. It should be appreciated that in some embodiments, an autonomous vehicle may be configured for water travel, hover travel, and or/air travel without departing from the spirit or the scope of the present disclosure. In general, an autonomous vehicle may be any suitable transport apparatus that may operate in an unmanned, driverless, self-driving, self-directed, and/or computer-controlled manner.

The embodiments may be implemented as hardware, firmware, and/or software logic embodied in a tangible, i.e., non-transitory, medium that, when executed, is operable to perform the various methods and processes described above. That is, the logic may be embodied as physical arrangements, modules, or components. For example, the systems of an autonomous vehicle, as described above with respect to FIG. 3, may include hardware, firmware, and/or software embodied on a tangible medium. In addition, an assessment system and a simulation system may include hardware, firmware, and/or software embodied on a tangible medium. A tangible medium may be substantially any computer-readable medium that is capable of storing logic or computer program code which may be executed, e.g., by a processor or an overall computing system, to perform methods and functions associated with the embodiments. Such computer-readable mediums may include, but are not limited to including, physical storage and/or memory devices. Executable logic may include, but is not limited to including, code devices, computer program code, and/or executable computer commands or instructions.

It should be appreciated that a computer-readable medium, or a machine-readable medium, may include transitory embodiments and/or non-transitory embodiments, e.g., signals or signals embodied in carrier waves. That is, a computer-readable medium may be associated with non-transitory tangible media and transitory propagating signals.

The steps associated with the methods of the present disclosure may vary widely. Steps may be added, removed, altered, combined, and reordered without departing from the spirit of the scope of the present disclosure. Therefore, the present examples are to be considered as illustrative and not restrictive, and the examples are not to be limited to the details given herein, but may be modified within the scope of the appended claims.

What is claimed is:

1. A method for validating a vision system, the method comprising:
   providing a vision testing medium at a first distance from the vision system;
   communicating a first information relating to the vision testing medium from a sensing apparatus to a first system;
   displaying, using the first system, a rendering of the vision testing medium based on the first information;
   obtaining, using the first system, at least a first indication of a visual acuity associated with the vision system;
   determining when the visual acuity at least meets a threshold level; and
   identifying the sensing apparatus as validated when the visual acuity at least meets the threshold level.

2. The method of claim 1 wherein the vision testing medium is a Landolt eye chart.

3. The method of claim 1 wherein the vision system includes at least one sensor mounted on an autonomous or semi-autonomous vehicle.

4. The method of claim 3 wherein the vision testing medium is a Landolt eye chart.

5. The method of claim 4 wherein displaying the rendering includes displaying the rendering on a display screen, and wherein obtaining the at least first indication includes assessing the rendering from a second distance away from the display screen.

6. The method of claim 5 wherein the first distance and the second distance form an effective distance of approximately twenty feet.

7. The method of claim 4 wherein obtaining the at least first indication of visual acuity includes obtaining the first indication and obtaining a second indication, wherein the first indication is obtained when the autonomous or semi-autonomous vehicle is in a first orientation with respect to the vision testing medium and the second indication is obtained when the autonomous or semi-autonomous vehicle is in a second orientation with respect to the vision testing medium.

8. Logic encoded in one or more tangible non-transitory, computer-readable media for execution and when executed operable to:
   provide a vision testing medium at a first distance from a vision system;

communicate a first information relating to the vision testing medium from a sensing apparatus to a first system;

display, using the first system, a rendering of the vision testing medium based on the first information;

obtain, using the first system, at least a first indication of a visual acuity associated with the vision system;

determine when the visual acuity at least meets a threshold level; and identify the sensing apparatus as validated when the visual acuity at least meets the threshold level.

9. The logic of claim 8 wherein the vision testing medium is a Landolt eye chart.

10. The logic of claim 8 wherein the vision system includes at least one sensor mounted on an autonomous or semi-autonomous vehicle.

11. The logic of claim 10 wherein the vision testing medium is a Landolt eye chart.

12. The logic of claim 11 wherein the logic operable to display the rendering includes logic operable to display the rendering on a display screen, and wherein the logic operable to obtain the at least first indication includes logic operable to assess the rendering from a second distance away from the display screen.

13. The logic of claim 12 wherein the first distance and the second distance form an effective distance of approximately twenty feet.

14. The logic of claim 11 wherein the logic operable to obtain the at least first indication of visual acuity includes logic operable to obtain the first indication and logic operable to obtain a second indication, wherein the first indication is obtained when the autonomous or semi-autonomous vehicle is in a first orientation with respect to the vision testing medium and the second indication is obtained when the autonomous or semi-autonomous vehicle is in a second orientation with respect to the vision testing medium.

15. A visual acuity assessment system comprising:
a sensing apparatus;
a vision system;
a vision testing medium, the vision testing medium being positioned at a first distance from the vision system; and
logic encoded in one or more tangible non-transitory, computer-readable media for execution and when executed operable to
communicate a first information relating to the vision testing medium from the sensing apparatus to the first system,
display, using the first system, a rendering of the vision testing medium based on the first information,
obtain, using the first system, at least a first indication of a visual acuity associated with the vision system,
determine when the visual acuity at least meets a threshold level, and
identifying the sensing apparatus as validated when the visual acuity at least meets the threshold level.

16. The visual acuity assessment system of claim 15 wherein the vision testing medium is a Landolt eye chart.

17. The visual acuity assessment system of claim 15 wherein the vision system includes at least one sensor mounted on an autonomous or semi-autonomous vehicle.

18. The visual acuity assessment system of claim 17 wherein the vision testing medium is a Landolt eye chart.

19. The visual acuity assessment system of claim 18 wherein the logic operable to display the rendering is operable to display the rendering on a display screen, and wherein the logic operable to obtain the at least first indication is operable to assess the rendering from a second distance away from the display screen.

20. The visual acuity assessment system of claim 19 wherein the first distance and the second distance form an effective distance of approximately twenty feet.

* * * * *